(12) United States Patent
Mori et al.

(10) Patent No.: US 9,790,242 B2
(45) Date of Patent: Oct. 17, 2017

(54) SURFACE TREATMENT METHOD, SURFACE TREATMENT AGENT, AND NOVEL COMPOUND

(75) Inventors: Kunio Mori, Morioka (JP); Yusuke Matsuno, Morioka (JP); Katsuhito Mori, Morioka (JP); Takahiro Kudo, Morioka (JP); Shuukichi Takii, Ayase (JP); Shigeru Michiwaki, Ayase (JP); Manabu Miyawaki, Ayase (JP); Masanori Yanai, Ayase (JP); Kouichi Kamiyama, Ayase (JP); Hitomi Chiba, Ayase (JP); Yasuyuki Masuda, Ayase (JP)

(73) Assignees: Kunio Mori, Morioka-shi (JP); Sulfur Chemical Laboratory, Inc., Morioka-shi (JP); Meiko Electronics Co., Ltd.

( * ) Notice: Subject to any disclaimer, the term of this patent is extended or adjusted under 35 U.S.C. 154(b) by 0 days.

(21) Appl. No.: 14/406,679

(22) PCT Filed: Aug. 31, 2012

(86) PCT No.: PCT/JP2012/072174
§ 371 (c)(1),
(2), (4) Date: Dec. 9, 2014

(87) PCT Pub. No.: WO2013/186941
PCT Pub. Date: Dec. 19, 2013

(65) Prior Publication Data
US 2015/0152124 A1 Jun. 4, 2015

(30) Foreign Application Priority Data
Jun. 11, 2012 (JP) .................... 2012-132410

(51) Int. Cl.
*B05D 3/02* (2006.01)
*C07F 7/18* (2006.01)

(52) U.S. Cl.
CPC ..... *C07F 7/1836* (2013.01); *Y10T 428/31678* (2015.04)

(58) Field of Classification Search
CPC .................. C07F 7/1836; Y10T 428/31678
(Continued)

(56) References Cited

U.S. PATENT DOCUMENTS 4,609,404 A * 9/1986 Marraccini ............. C09B 1/467
106/417
4,874,858 A * 10/1989 Magistro ................. C03C 25/40
544/196
6,893,679 B2 * 5/2005 Jahromi .................. C08J 7/065
427/248.1

FOREIGN PATENT DOCUMENTS

CN 101433826 A 5/2009
EP 0 103 986 A2 3/1984
(Continued)

OTHER PUBLICATIONS

Korean Office Action dated Jun. 26, 2015 in Patent Application No. 10-2014-7033203 (without English Translation).
Extended European Search Report dated Jan. 15, 2016 in Patent Application No. 12878807.2.
Anna Iuliano, et al., "The s-triazine moiety as a scaffold for connecting different chiral auxiliaries: synthesis of new biselector CSPs for enantioselective chromatography" Tetrahedron: Asymmetry, vol. 14, No. 10, XP004439170, May 16, 2010, pp. 1345-1353.
Cristina Lecci, et al., "Synthesis and evaluation of a new biselector s-triazine based chiral stationary phase for enantioselective HPLC: potentiality of the approach and perspectives" Biomedical Chromatography, vol. 19, No. 6, XP055233966, Jan. 1, 2005, pp. 439-446.
Margandan Bhagiyalakshmi, et al., "Development of TREN dendrimers over mesoporous SBA-15 for $CO_2$ adsorption" Applied Surface Science, vol. 256, No. 22, XP027092487, Sep. 1, 2010, pp. 6660-6666.
(Continued)

Primary Examiner — Robert S Walters, Jr.
(74) Attorney, Agent, or Firm — Oblon, Mcclelland, Maier & Neustadt, L.L.P.

(57) ABSTRACT

A surface treatment technique having excellent adhering function, excellent reacting function and rich diversity is provided. The surface treatment includes applying a solution containing compound (α) to a substrate and thus providing compound (α) thereon, wherein: the compound (α) is at least one of Formula [IV] and Formula [V]:

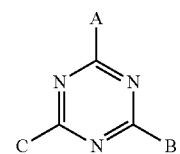

Formula [IV]

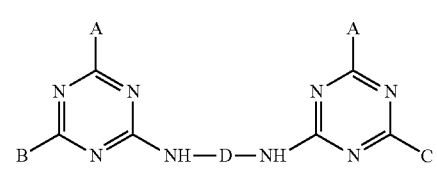

Formula [V]

wherein A is —N($R^a$)$R^b$—Si($R^c$)$_n$(O$R^d$)$_{3-n}$, or —N{$R^b$—Si($R^c$)$_n$(O$R^d$)$_{3-n}$}$_2$, B is —N($R^e$)$R^f$(NH$_2$)$_m$, or —N{$R^f$(NH$_{2\{m\}}$)$_2$, C is A, B, or —N($R^g$)$R^h$, D is $R^i$ and wherein each of $R^a$, $R^e$, and $R^g$ is independently H or a hydrocarbon group, $R^b$, $R^c$, $R^d$, $R^f$, $R^h$, and $R^i$ are hydrocarbon groups, n is 0, 1, or 2, and m is 1 or 2.

7 Claims, No Drawings

(58) Field of Classification Search
USPC .......................................................... 427/387
See application file for complete search history.

(56) References Cited

FOREIGN PATENT DOCUMENTS

| EP | 0 103 986 A3 | 3/1984 |
|---|---|---|
| JP | 02-006490 A | 1/1990 |
| JP | 2006-241120 A | 9/2006 |
| JP | 2007-119752 A | 5/2007 |
| JP | 2008-50541 A | 3/2008 |
| JP | 2010-280813 A | 12/2010 |
| WO | WO 2006/128732 A1 | 12/2006 |
| WO | WO 2012/043631 A1 | 4/2012 |
| WO | WO 2012/046651 A1 | 4/2012 |

OTHER PUBLICATIONS

Chanfeng Zhoa, et al., "Methods of attaching biological compounds to solid supports using triazine" Database CA, Chemical Abstracts Service, Caesar Accession No. 1620, Database Accession No. 2006:579267, XP002752571, 2006, 2 Pages.

Xinmiao Liang, et al., "Amide-like reversed-phase stationary phase and its production method" Database CA, Chemical Abstracts Service, Caesar Accession No. 1614, Database Accession No. 2009:634413, XP002752572, 2009, 1 Page.

Weiou Liu, et al., "Silyl-substituted melamine curing agent for epoxy resin and its preparation method and application of" Database CA, Chemical Abstracts Service, Caesar Accession No. 1610, Database Accession No. 2010:669633, XP002752573, 2010, 5 Pages.

International Search Report dated Dec. 11, 2012 in PCT/JP2012/072174 Filed Aug. 31, 2012.

Mahendra P. Kapoor, et al, "Catalysis by mesoporous dendrimers", Topics in Catalysis, vol. 52, No. 6-7, 2009, pp. 634-642.

Kunio Mori, "The 21th century adhesion technology Molecular adhesives", Journal of the Adhesion Society of Japan, vol. 43, No. 6, 2007, pp. 242-248 (with English language translation).

Kunio Mori, et al., "Sixivalent chromate-free resin plating—a molecular adhesion method", Journal of the Surface Finishing Society of Japan, vol. 59. No. 5, 2008, pp. 299-304 (with English language translation).

Taiwanese Search Report dated Oct. 28, 2014 in Patent Application No. 102120054 (with English Translation of Category of Cited Documents).

European Office Action dated Mar. 13, 2017 in Patent Application No. 12 878 807.2.

Maqbool Hussain, et al., "Synthesis of novel stilbene-alkoxysilane fluorescent brighteners, and their performance on cotton fiber as fluorescent brightening and ultraviolet absorbing agents" Dyes and Pigments, vol. 92, 2012, XP028106507 A, pp. 1231-1240.

* cited by examiner

SURFACE TREATMENT METHOD, SURFACE TREATMENT AGENT, AND NOVEL COMPOUND

TECHNICAL FIELD

The present invention relates to a technology of surface treatment.

BACKGROUND ART

Man has manufactured various types of products using different substances (materials). The materials are classified to metal materials, ceramic materials, high polymerized materials, and composite materials made of combinations of the aforementioned materials. Each of the materials has a unique property. The property shows characteristics of the products. It is possible to form metals and ceramics solely into products. However, alloys and multi-element ceramics are made in a manner that more than two kinds of elements are dissolved to be mixed. The high polymerized materials are composed of (synthesized with) elements such as C, H, O, N, X (halogen), P, and S, as required. There are tons of elements which can be used for producing the high polymerized materials.

An attribute of the material is shown by a sum of a bulk attribute and a surface attribute. The bulk attribute is almost determined according to a kind and/or a composition of the material. The surface attribute is not always the same even when the kind and/or the composition of elements are the same. The surface attribute changes according to time as well as an external field environment based on a law of Gibbs' free energy ($\Delta G = \Delta H - T\Delta S$, $\Delta H$: enthalpy change, T: absolute temperature, $\Delta S$: entropy change). If the external field environment includes, for example, oxygen, humidity, and ultraviolet rays, the surface of the material chemically changes to be another substance (i.e., to have another attribute) from moment to moment.

The change of the surface of the material in the natural world puts a hard obstacle to the improvement of manufacturing of products using surface functions thereof. The obstacle varies according to the kinds of the surface functions. However, it is at least apparent that a surface property of a product differs between yesterday and today. A material dependency derives from a surface nature which the material has as its unique attribute. Today, this is unavoidable. However, if construction of a concept of identification of the changes at a certain point of time realizes a material independency, it becomes possible to improve the manufacturing of products based on the concept. This will bring us a bright future in this twenty-first century.

The identification of the surfaces of the materials is achieved according to the following steps. For example, if it becomes possible to make films (thin films) having the same chemical composition and surface property at any time for any material, the identification of the surfaces of the materials will be achieved by a surface treatment method capable of providing such films (thin films). The inventor of the present invention names such agent an identical surface making-functionalizing agent. We sometimes call the identical surface making-functionalizing agent simply as a surface treatment agent. When the identical surface making-functionalizing agent for identifying the surfaces of the materials is brought into contact with the materials (e.g., metal materials, ceramic materials, high polymerized materials, organic solids, and other composite materials), the identical surface making-functionalizing agent tightly adheres to the surfaces of the materials or chemically bonds to (reacts with) the surfaces of the materials. As a result, the materials come to have the same properties on their surfaces independent from the kinds of their materials. In other words, differences of the surface properties are minimized as much as possible between materials. An agent producing the above described effect is the identical surface making-functionalizing agent.

The identical surface making-functionalizing agent has a function of tightly adhering (or bonding) to the surface of the material and thereby forming a film (thin film) thereon. The identical surface making-functionalizing agent tightly adhered (or bonded) to the surface of the material comes to have a function of reacting with other functional groups. The identical surface making-functionalizing agent has a function of effectively working on many kinds of materials. In sum, the identical surface making-functionalizing agent is rich in diversity. We call the agent having such property, specifically, as the identical surface making-functionalizing agent.

Some of the conventional surface treatment agents have a function of, for example, adhering to a surface of a material. However, such conventional surface treatment agents are sometimes poor in reaction. Or, such conventional surface treatment agents sometimes lack diversity. For example, such conventional surface treatments are applicable to a material A but are not applicable to a material B. In other words, such conventional surface treatments are only applicable to materials of a limited range (lacks diversity).

CITATION LIST

Patent Literature

[Patent Literature 1]
  WO2012/043631 A1

Non-Patent Literature

[Non Patent Literature 1]
  Journal of the Adhesion Society of Japan: Kunio MORI; vol. 43 (6); 242-248 (2007)
[Non Patent Literature 2]
  Journal of the Surface Finishing Society of Japan: Kunio MORI; vol. 59 (5); 299-304 (2008)
[Non Patent Literature 3]
  Journal of Top Catal (2009) 52: 634-642

SUMMARY OF INVENTION

Technical Problem

The conventional surface treatment agents were not effective to materials of a wide range.

It seems that Non-patent Literature 3 discloses something similar to a material treated by the surface treatment agent of the present invention. However, Non-patent Literature 3 is silent on what is disclosed in the present invention.

A problem to be solved by the present invention is to provide a surface treatment technology having an adhesion function and a reactive function and, further, being rich in diversity.

Solution to Problem

The above problem is solved by providing a surface treatment method in which a solution containing a compound α is applied to a substrate to provide the compound α thereon:

wherein the compound α contains at least
an M-OH group and/or an M-OH yielding group (M: metal element),
an amino group, and
a triazine ring;
wherein there are one or more M-OH groups and/or M-OH yielding groups (M: metal element);
wherein there are one or more triazine rings;
wherein at least one amino group of amino groups is indirectly bonded to C of the triazine ring;
wherein the indirectly bonded amino group is positioned at least at a terminal; and
wherein there are one or more amino groups at terminal.

The above problem is solved by providing a surface treatment method in which a compound α is evaporated to be provided on a substrate:
wherein the compound α contains at least
an M-OH group and/or an M-OH yielding group (M: metal element),
an amino group, and
a triazine ring;
wherein there are one or more M-OH groups and/or M-OH yielding groups (M: metal element);
wherein there are one or more triazine rings;
wherein at least one amino group of amino groups is indirectly bonded to C of the triazine ring;
wherein the indirectly bonded amino group is positioned at least at a terminal; and
wherein there are one or more amino groups at terminal.

The above problem is solved by providing the surface treatment method wherein, preferably before being provided with the compound α, the substrate is subjected to at least one or more treatment selected from the group consisting of cleaning treatment, corona discharge treatment, plasma discharge treatment, ultraviolet ray irradiation, acid treatment, alkaline treatment, steam treatment, and chemical conversion coating.

The above problem is solved by providing the surface treatment method wherein, for example, after being provided with the compound α, the substrate is subjected to heating treatment.

The above problem is solved by providing a surface treatment agent to be used in the surface treatment method:
wherein the surface treatment agent is a compound α or contains the compound α;
wherein the compound α contains at least
an M-OH group and/or an M-OH yielding group (M: metal element),
an amino group, and
a triazine ring;
wherein there are one or more M-OH groups and/or M-OH yielding groups (M: metal element);
wherein there are one or more triazine rings;
wherein at least one amino group of amino groups is indirectly bonded to C of the triazine ring;
wherein the indirectly bonded amino group is positioned at least at a terminal; and
wherein there are one or more amino groups at terminal.

Preferably, the amino group bonded to the terminal is a primary amino group.

Preferably, the M-OH group and/or the M-OH yielding group (M: metal element) are alkoxysilyl groups.

Preferably, the compound α is a compound represented by the following General Formula [I]. More preferably, the compound α is a compound represented by the following General Formula [II] or [III].

$$\{(NR^1R^2)_aX-Q\}_bY(W)_c\{Z(V-M(R^3)_n(OR^4)_{3-n}\}_d \quad \text{General Formula [I]}$$

(In the formula [I], each of $R^1$, $R^2$, $R^3$, and $R^4$ is H or a functional group. $R^1$, $R^2$, $R^3$, and $R^4$ may be the same or may be different from one another. The X, Z, Q, and V are linking groups. There is a case where the formula does not include X, Z, and/or Q (however, except for a case where the formula includes neither X, Z, nor Q). Y is a skeletal formula. The skeletal formula has a triazine ring ($C_3N_3$). —$NH_2$ and —$N_3$ are not directly bonded to the triazine ring. W is a functional group other than $\{Z(V-M(R^3)_n(OR^4)_{3-n})\}$. M is at least one selected from the group consisting of Si, Al, and Ti. a is an integer equal to or more than 1, b is 1 or 2, c is 0 or 1, d is 1 or 2, b+c+d=3, and n is 0, 1, or 2.)

$$\{(NR^1R^2)_aX-Q\}_bY\{NH(CH_2)_mSi(R^3)_n(OR^4)_{3-n}\}_e \quad \text{General Formula [II]}$$

$$\{(NR^1R^2)_aX-Q\}_bY[N\{(CH_2)_mSI(R^3)_n(OR^4)_{3-n}\}_2]_e \quad \text{General Formula [III]}$$

(In the formulas [II] and [III], each of $R^1$, $R^2$, $R^3$, and $R^4$ is H or a functional group. $R^1$, $R^2$, $R^3$, and $R^4$ may be the same or may be different from one another. X and Q are linking groups. There is a case where the formula does not include the linking group X or Q (however, except for a case where the formula include neither X nor Q). Y is a skeletal formula. The skeletal formula has a triazine ring ($C_3N_3$). —$NH_2$ and —$N_3$ are not directly bonded to the triazine ring. a is an integer equal to or more than 1, b is 1 or 2, e is 1 or 2, b+e=3, m is an integer equal to or more than 1, and n is 0, 1, or 2.)

Preferably, the compound α is at least one selected from the group consisting of N,N'-bis(2-aminoethyl)-6-(3-triethoxysilylpropyl)amino-1,3,5-triazine-2,4-diamine, 6-(3-triethoxysilylpropyl)amino-2,4-dihydrazinyl-1,3,5-triazine, 2-(N,N'-di-3-triethoxysilylpropyl)amino-4,6-di(2-aminoethyl)amino-1,3,5-triazine, 2-(2-aminoethyl)amino-4,6-di(3-triethoxysilylpropyl)amino-1,3,5-triazine, 6-(2-aminoethyl)amino-2,4-bis(methylethylketoxyminosilyl)propylamino-1,3,5-triazine, 6-(2-aminoethyl)amino-2,4-di(triisopropoxysilyl)propylamino-1,3,5-triazine, 6-(2-aminoethyl)amino-2,4-di(triacetoxysilyl)propylamino-1,3,5-triazine, 6-(2-aminoethyl)amino-2,4-di(triisopropenoxysilyl)propylamino-1,3,5-triazine, 6-(2-aminoethyl)amino-2,4-di(triisopropoxysilyl)propylamino-1,3,5-triazine, 6-(2-aminoethyl)amino-2,4-di(tribenzoxysilyl)propylamino-1,3,5-triazine, 6-(2-aminoethyl)amino-2,4-bis(triethoxysilylhexyamino-1,3,5-triazine, 6-(2-aminoethyl)amino-2,4-bis(triethoxysilyldodecyl)amino-1,3,5-triazine, 2,4-di(2-aminoethyl)amino-6-bis(methylethylketoxyaminosilyl)propylamino-1,3,5-triazine, 2,4-di(2-aminoethyl)amino-6-di(triisopropoxysilyl)propylamino-1,3,5-triazine, 2,4-di(2-aminoethyl)amino-6-di(triacetoxysilyl)propylamino-1,3,5-triazine, 2,4-di(2-aminoethyl)amino-6-di(triisopropenoxysilyl)propylamino-1,3,5-triazine, 2,4-di(2-aminoethyl)amino-6-di(triisopropoxysilyl)propylamino-1,3,5-triazine, 2,4-di(2-aminoethyl)amino-6-di(tribenzoxysilyl)propylamino-1,3,5-triazine, 2,4-di(2-aminoethyl)amino-6-bis(triethoxysilylhexylamino)-1,3,5-triazine, 2,4-di(2-aminoethyl)amino-6-bis(triethoxysilylpropyl)amino-1,3,5-triazine, N,N'-bis(2-dimethylaminoethyl)-6-(3-triethoxysilylpropyl)amino-1,3,5-triazine-2,4-diamine, N,N'-bis(2-aminohexyl)-6-(3-triethoxysilylpropyl)amino-1,3,5-triazine-2,4-diamine, N,N'-bis{2-[bis-(2-aminoethyl)amino]ethyl}-6-(3-triethoxysilylpropyl)amino-1,3,5-triazine-2,4-diamine, and N,N'-bis(12-aminododecyl)-6-(3-triethoxysilylpropyl)amino-1,3,5-triazine-2,4-diamine.

The above problem is solved by providing a novel compound characterized in that the compound is represented by the above described General Formula [I].

The above problem is solved by a novel compound characterized in that the compound is represented by the above described General Formula [II].

The above problem is solved by a novel compound characterized in that the compound is represented by the above described General Formula [III].

Advantageous Effect of Invention

The present invention ensures obtainment of a material having a film on its surface, the film being rich in adherence, reactivity, and diversity.

DESCRIPTION OF EMBODIMENTS

A first invention is directed to a novel compound. Preferably, the first invention is directed to a novel compound capable of working as an identical surface making-functionalizing agent. The novel compound is represented by the General Formula [I]. In the General Formula [I], each of $R^1$, $R^2$, $R^3$, and $R^4$ is H or a functional group. The functional group contains at least one element selected from the group consisting of elements of, for example, C, O, N, and S. Preferably, the functional group is a hydrocarbon group. Preferably, the hydrocarbon group is an aliphatic hydrocarbon group. Preferably, the aliphatic hydrocarbon group is an alkyl group. The hydrocarbon group may have a straight structure or may have a branched structure. Preferably, the hydrocarbon group has a carbon number of 1 to 10. Each of the linking groups X, Z, Q, and V contains at least one element selected from the group consisting of elements of, for example, C, O, N, and S. Preferably, the linking groups X and V are hydrocarbon groups. In particular, each of the hydrocarbon groups is a hydrocarbon group having a carbon number of 1 to 18. Preferably, the hydrocarbon group is an aliphatic hydrocarbon group. Preferably, the aliphatic hydrocarbon group is an alkyl group. The hydrocarbon group may have a straight structure or may have a branched structure. The hydrocarbon group may contain —S—, —O—, —NHCO—, —N<, and/or —NH—. Preferably, the linking groups Q and Z are —NH—, —N<, —O—, —S—, or —NHCO—. Preferably, the functional group W is —NR$^5$R$^6$, —NHOH, —NH(CH$_2$)$_p$OH, —N((CH$_2$)$_p$OH)$_2$, or —N(CH$_2$)$_p$NH—Y(Z(V-M(R$^3$)$_p$(OR$^4$)$_{3-n}$)(Q(X—NR$^1$R$^2$)). Each of $R^1$, $R^2$, $R^3$, and $R^4$ is H or a functional group. $R^1$, $R^2$, $R^3$, and $R^4$ may be the same or may be different from one another. Each of the functional groups contains at least one element selected from the group consisting of elements of, for example, C, O, N, and S. Preferably, the functional group is a hydrocarbon group. In particular, the hydrocarbon group is a hydrocarbon group having a carbon number of 1 to 10. Preferably, the hydrocarbon group is an aliphatic hydrocarbon group. Specifically, the hydrocarbon group is an alkyl group. Each of $R^5$ and $R^6$ is a hydrocarbon group. In particular, the hydrocarbon group is a hydrocarbon group having a carbon number of 1 to 10. Preferably, the hydrocarbon group is an aliphatic hydrocarbon group. Preferably, the aliphatic hydrocarbon group is an alkyl group. X, Z, Q, and V are linking groups. There is a case where the formula does not include the linking group X, Z, and/or Q (however, except for a case where the formula includes neither X, Z, nor Q). Each of the linking groups X, Z, Q, and V contains at least one element selected from the group consisting of elements of, for example, C, O, N, and S. Preferably, each of the linking groups X and V is a hydrocarbon group. In particular, the hydrocarbon group is a hydrocarbon group having a carbon number of 1 to 18. Preferably, the hydrocarbon group is an aliphatic hydrocarbon group. Preferably, the aliphatic hydrocarbon group is an alkyl group. The hydrocarbon group may have a straight structure or may have a branched structure. The hydrocarbon group may contain —S—, —O—, —NHCO—, —N<, and/or —NH—. Preferably, the linking groups Q and Z are —NH—, —N<, —O—, —S—, or —NHCO—. Y is a skeletal formula. The skeletal formula contains a triazine ring (C$_3$N$_3$). Preferably, —NH$_2$ and —N$_3$ (azide group) are not directly bonded to the triazine ring. M is at least one selected from the group consisting of Si, Al, and Ti. p is an integer equal to or more than 1. Specifically, p is an integer from 1 to 12. n is 0, 1, or 2. Preferably, a is an integer equal to or less than 8.

The novel compound is specifically represented by the General Formula [II] or the General Formula [III]. In the General Formulas [II] and [III], each of $R^1$, $R^2$, $R^3$, and $R^4$ is H or a functional group. Preferably, the functional group is a hydrocarbon group. Preferably, the hydrocarbon group is an aliphatic hydrocarbon group. Preferably, the aliphatic hydrocarbon group is an alkyl group. The hydrocarbon group may have a straight structure or may have a branched structure. Preferably, the hydrocarbon group has a carbon number of 1 to 10. Each of the linking groups X and Q contains at least one element selected from the group consisting of elements of, for example, C, O, N, and S. Preferably, the linking group X is a hydrocarbon group. Preferably, the hydrocarbon group is an aliphatic hydrocarbon group. Preferably, the aliphatic hydrocarbon group is an alkyl group. The hydrocarbon group may have a straight structure or may have a branched structure. Preferably, the hydrocarbon group has a carbon number of 1 to 18. The hydrocarbon group may contain —S—, —O—, —NHCO—, —N<, and/or —NH—. Preferably, the linking group Q is —NH—, —N<, —O—, —S—, or —NHCO—. In the present invention, the triazine ring may be a heterocyclic ring containing C$_3$N$_3$. In the present invention, a meaning of the triazine ring includes a melamine structure (C$_3$N$_3$N$_3$H$_3$) in a broad sense. Preferable triazine ring is a 1,3,5-triazine ring. Preferably, a is an integer equal to or less than 8. Preferably, m is an integer from 1 to 18. Preferably, —NH$_2$ and —N$_3$ (azide group) are not directly bonded to the triazine ring. In the General Formulas [I], [II], and [III], preferably, each of the functional groups {(NR$^1$R$^2$)$_a$X-Q}, W, {Z(V-M(R$^3$)$_n$(OR$^4$)$_{3-n}$)}, {NH(CH$_2$)$_m$Si(R$^3$)$_n$(OR$^4$)$_{3-n}$}, and N{(CH$_2$)$_m$Si(R$^3$)$_n$(OR$^4$)$_{3-n}$}$_2$ is bonded to C of a skeletal formula (Y) of the triazine ring. Specifically, each of {NH(CH$_2$)$_m$Si(R$^3$)$_n$(OR$^4$)$_{3-n}$} and N{(CH$_2$)$_m$Si(R$^3$)$_n$(OR$^4$)$_{3-n}$}$_2$ is bonded to the skeletal formula Y via the bonding (C—N bonding) between N and C of the skeletal formula Y. Each of {(NR$^1$R$^2$)$_a$X-Q} and {Z(V-M(R$^3$)$_n$(OR$^4$)$_{3-n}$)} is bonded to the skeletal formula Y via the bonding (i.e., C—N bonding, C—C bonding, or C—O bonding) between elements of the functional groups at terminals of X, Q, Z, and V and C of the skeletal formula (Y).

Preferably, in the novel compound, the amino group positioned at the terminal is a primary amino group.

Examples of the novel compound include
N,N'-bis(2-aminoethyl)-6-(3-triethoxysilylpropyl)amino-1,3,5-triazine-2,4-diamine;
6-(3-triethoxysilylpropyl)amino-2,4-dihydrazinyl-1,3,5-triazine;
2-(N,N'-di-3-triethoxysilylpropyl)amino-4,6-di(2-aminoethyl)amino-1,3,5-triazine;
2-(2-aminoethyl)amino-4,6-di(3-triethoxysilylpropyl)amino-1,3,5-triazine;
6-(2-aminoethyl)amino-2,4-bis(methylethylketoxyminosilyl)propylamino-1,3,5-triazine;

6-(2-aminoethyl)amino-2,4-di(triisopropoxysilyl)propylamino-1,3,5-triazine;
6-(2-aminoethyl)amino-2,4-di(triacetoxysilyl)propylamino-1,3,5-triazine;
6-(2-aminoethyl)amino-2,4-di(triisopropenoxysilyl)propylamino-1,3,5-triazine;
6-(2-aminoethyl)amino-2,4-di(triisopropoxysilyl)propylamino-1,3,5-triazine;
6-(2-aminoethyl)amino-2,4-di(tribenzoxysilyl)propylamino-1,3,5-triazine;
6-(2-aminoethyl)amino-2,4-bis(triethoxysilylhexyl)amino-1,3,5-triazine;
6-(2-aminoethyl)amino-2,4-bis(triethoxysilyldodecyl)amino-1,3,5-triazine;
2,4-di(2-aminoethyl)amino-6-bis(methylethylketoxyminosilyl)propylamino-1,3,5-triazine;
2,4-di(2-aminoethyl)amino-6-bis(methylethylketoxyminosilyl)propylamino-1,3,5-triazine;
2,4-di(2-aminoethyl)amino-6-di(triisopropoxysilyl)propylamino-1,3,5-triazine;
2,4-di(2-aminoethyl)amino-6-di(triacetoxysilyl)propylamino-1,3,5-triazine;
2,4-di(2-aminoethyl)amino-6-di(triisopropenoxysilyl)propylamino-1,3,5-triazine;
2,4-di(2-aminoethyl)amino-6-di(triisopropoxysilyl)propylamino-1,3,5-triazine;
2,4-di(2-aminoethyl)amino-6-di(tribenzoxysilyl)propylamino-1,3,5-triazine;
2,4-di(2-aminoethyl)amino-6-bis(triethoxysilylhexylamino)-1,3,5-triazine;
2,4-di(2-aminoethyl)amino-6-bis(triethoxysilylpropyl)amino-1,3,5-triazine;
N,N'-bis(2-dimethylaminoethyl)-6-(3-triethoxysilylpropyl)amino-1,3,5-triazine-2,4-di amine;
N,N'-bis(2-aminohexyl)-6-(3-triethoxysilylpropyl)amino-1,3,5-triazine-2,4-diamine;
N,N'-bis{2-[bis-(2-aminoethyl)amino-]ethyl}-6-(3-triethoxysilylpropyl)amino-1,3,5-triazine-2,4-diamine; and
N,N'-bis(12-aminododecyl)-6-(3-triethoxysilylpropyl)amino-1,3,5-triazine-2,4-diamine. Only typical examples are shown above. As a matter of course, it is possible to give many other compounds in addition to the above examples. However, many other examples are omitted here because of space limitations.

The novel compound is represented by, for example, the following General Formula [IV] or [V].

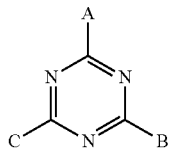

General Formula [IV]

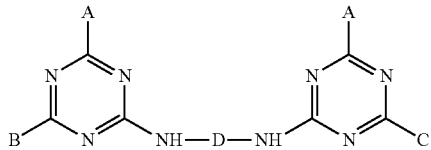

General Formula [V]

In the above General Formulas [IV] and [V], A, B, C, and D are, for example, the following groups.

$A = -N(R^a)R^b - Si(R^c)_n(OR^d)_{3-n}$, or $-N\{R^b - Si(R^c)_n(OR^d)_{3-n}\}_2$ $B = -N(R^e)R^f(NH_2)_m$, or $-N\{R^f(NH_2)_m\}_2$ $C = A$, $B$, or $-N(R^g)R^h$ $D = R^i$

[Here, each of $R^a$, $R^e$, and $R^g$ is H or a hydrocarbon group. $R^b$, $R^c$, $R^d$, $R^f$, $R^h$, and $R^i$ are hydrocarbon groups. n is 0, 1, or 2. m is 1 or 2. There is a case where the hydrocarbon group contains —S—, —O—, —NHCO—, —N<, and —NH—, or there is a case where the hydrocarbon group does not contain —S—, —O—, —NHCO—, —N<, or —NH—. There is a case where the hydrocarbon group contains a substituent group, or there is a case where the hydrocarbon group does not contain the substituent group.]

Preferably, the hydrocarbon group is an aliphatic hydrocarbon group. Preferably, the aliphatic hydrocarbon group is an alkyl group.

Preferably, the $R^a$ has a carbon number of 1 to 12. Preferably, the $R^b$ has a carbon number of 1 to 12. Preferably, the $R^c$ has a carbon number of 1 to 6. Preferably, the $R^d$ has a carbon number of 1 to 6. Preferably, the $R^e$ has a carbon number of 1 to 12. Preferably, the $R^f$ has a carbon number of 1 to 12. Preferably, the $R^g$ has a carbon number of 1 to 12. Preferably, the $R^h$ has a carbon number of 1 to 12. Preferably, the $R^i$ has a carbon number of 1 to 12.

Some specific examples of A, B, C, and D are listed below. However, this should not be construed in a limiting sense.

$\{A = -NH-(CH_2)l-Si(O(CH_2)_n(CH_3))_3$, $-N(CH_2)l-Si(O(CH_2)_n(CH_3))_3$, $-NH-(CH_2)l-Si(CH_3)(O(CH_2)_n(CH_3))_2$, or $-NH-C_6H_4-O-(CH_2)l-Si(O(CH_2)_n(CH_3))_3$ $B = -NH-(CH_2)l(NH_2)$, or $-N((CH_2)l(NH_2))_2$ $C = A$, $B$, $-NH(CH_2)lCH_3$, $-N((CH_2)lCH_3)_2$, or $-N(CH_2CH=CH_2)((CH_2)_mCH_3)$ $D = -(CH_2)_p-$ l, m, n, and p: an integer equal to or more than 1}

$\{A = -NH-(CH_2)l-Si(O(CH_2)_n(CH_3))_3$, $-NH-(CH_2)l-Si(CH_3)(O(CH_2)_n(CH_3))_2$, or $-NH-C_6H_4-O-(CH_2)l-Si(O(CH_2)_n(CH_3))_3$, $B = -NH-(CH_2)l(NH_2)$, or $-N((CH_2)l(NH_2))_2$ $C = A$, or $B$ $D = -(CH_2)_p-$ l, n, and p: an integer equal to or more than 1}

$\{A = -N((CH_2)l-Si(O(CH_2)_n(CH_3))_3$, $-N((CH_2)l-Si(CH_3)(O(CH_2)_n(CH_3))_2)_2$, or $-N-(C_6H_4-O-(CH_2)l-Si(O(CH_2)_n(CH_3)_2)((CH_2)_pCH_3)$ $B = -NH-(CH_2)l(NH_2)$, or $-N((CH_2)l(NH_2))_2$ $C = A$, or $B$ $D = -(CH_2)_p-$ l, n, and p: an integer equal to or more than 1}

A second invention is directed to a surface treatment agent. More specifically, the second invention is directed to a surface treatment agent that can also be referred to as an identical surface making-functionalizing agent. The surface treatment agent is an agent for the use of bonding by, for example, the compound α. The surface treatment agent is an agent for the use of chemical reaction or physical absorption by, for example, the compound α. The surface treatment agent is the compound α. Alternatively, the surface treatment agent is an agent containing the compound α. The compound α contains at least an M-OH group and/or an M-OH yielding group (M: metal element), an amino group, and a triazine ring. Preferably, the M-OH group and/or the M-OH yielding group are bonded to carbon atoms of the triazine ring directly or indirectly (via linking groups). Preferably, the amino group is bonded to a carbon atom (C) of the triazine ring directly or indirectly (via a linking group). At least one amino group of amino groups is indirectly bonded to the carbon atom (C) of the triazine ring. The indirectly bonded amino group is positioned at least at a terminal. There are one or more amino groups at terminal. For example, there are one or two amino groups. There are one or more M-OH groups and/or M-OH yielding groups (M: metal element). Preferably, M is Si, Al, or Ti. There are one or more triazine rings. For example, there are one or two triazine rings. Preferably, the amino group bonded to the terminal is a primary amino group. More preferably, the M-OH group and/or the M-OH yielding group (M: metal element) are alkoxysilyl groups. When the compound α containing the primary amino group and the alkoxysilyl group in a monomolecular thereof contacts a material selected from the group consisting of metal materials, ceramic materials, and high polymerized materials, the compound α is tightly bonded to a surface of the selected material by the chemical bonding (or tight absorption) caused by reaction between these materials and the compound α. For example, a case where the compound α is not vaporized while it is left for a long time under super high vacuum, for example, beyond $10^{-6}$ Pa, is hereinafter referred to as tight adherence (absorption). Of course, no vaporization occurs even while the compound α is chemically bonding (reacting). Such situation can be analyzed by an XPS. The compound containing both of the primary amino group and the alkoxysilyl group in a monomolecular thereof is available in market in the name of the silane coupling agent. However, the conventional silane coupling agent does not stick to (react with) any one of the metal materials, the ceramic materials, and the high polymerized materials. For example, as the kinds of the materials change, the kinds of the silane coupling agents and treatment conditions change. Specifically, in a case of materials (e.g., high polymerized materials) which has little —OH on its surface, the tight adherence and the chemical bonding hardly occur. In other words, a silane coupling agent that is rich enough in diversity and thus is solely useful for many cases has not been developed yet. In sum, a silane coupling agent having features defined in the present invention is not developed yet. In this point, the compound α of the present invention totally differs from the conventional silane coupling agent. Preferable compound α is the compound represented by the General Formula [I]. More preferable compound α is the compound represented by the General Formula [II] or [III]. For example, further preferable compound α is the compound represented by the General Formula [IV] or [V]. Preferably, —$NH_2$ and —$N_3$ (azide group) are not directly bonded to the triazine ring. Preferably, the amino group positioned at terminal is a primary amino group. Specifically, examples of the compound α include N,N'-bis(2-aminoethyl)-6-(3-triethoxysilylpropyl)amino-1, 3,5-triazine-2,4-diamine;
6-(3-triethoxysilylpropyl)amino-2,4-dihydrazinyl-1,3,5-triazine;
2-(N,N'-di-3-triethoxysilylpropyl)amino-4,6-di(2-amino ethyl)amino-1,3,5-triazine;
2-(2-aminoethyl)amino-4,6-di(3-triethoxysilylpropyl) amino-1,3,5-triazine;
6-(2-aminoethyl)amino-2,4-bis(methylethylketoxyminosilyl)propylamino-1,3,5-triazine;
6-(2-aminoethyl)amino-2,4-di(triisopropoxysilyl)propylamino-1,3,5-triazine;
6-(2-aminoethyl)amino-2,4-di(triacetoxysilyl)propylamino-1,3,5-triazine;
6-(2-aminoethyl)amino-2,4-di(triisopropenoxysilyl)propylamino-1,3,5-triazine;
6-(2-amino ethyl)amino-2,4-di(triisopropoxysilyl)propylamino-1,3,5-triazine;
6-(2-aminoethyl)amino-2,4-di(tribenzoxysilyl)propylamino 1,3,5-triazine;
6-(2-aminoethyl)amino-2,4-bis(triethoxysilylhexyl)amino-1,3,5-triazine;
6-(2-aminoethyl)amino-2,4-b is(triethoxysilyl dodecyl) amino-1,3,5-triazine;
2,4-di(2-aminoethyl)amino-6-bis(methylethylketoxyminosilyl)propylamino-1,3,5-triazine;
2,4-di(2-aminoethyl)amino-6-bis (methylethylketoxyminosilyl)propylamino-1,3,5-triazine;
2,4-di(2-aminoethyl)amino-6-di(triisopropoxysilyl)propylamino-1,3,5-triazine;
2,4-di(2-aminoethyl)amino-6-di(triacetoxysilyl)propylamino-1,3,5-triazine;
2,4-di(2-aminoethyl)amino-6-di(triisopropenoxysilyl)propylamino-1,3,5-triazine;
2,4-di(2-aminoethyl)amino-6-di(triisopropoxysilyl)propylamino-1,3,5-triazine;
2,4-di(2-aminoethyl)amino-6-di(tribenzoxysilyl)propylamino-1,3,5-triazine;
2,4-di(2-aminoethyl)amino-6-bis(triethoxysilylhexylamino)-1,3,5-triazine;
2,4-di(2-aminoethyl)amino-6-bis(triethoxysilylpropyl) amino-1,3,5-triazine;
N,N'-bis(2-dimethylaminoethyl)-6-(3-triethoxysilylpropyl) amino-1,3,5-triazine-2,4-diamine;
N,N'-bis(2-aminohexyl)-6-(3-triethoxysilylpropyl)amino-1, 3,5-triazine-2,4-diamine;
N,N'-bis{2-[bis-(2-aminoethyl)amino-]ethyl}-6-(3-triethoxysilylpropyl)amino-1,3,5-triazine-2,4-diamine; and
N,N'-bis(12-aminododecyl)-6-(3-triethoxysilylpropyl) amino-1,3,5-triazine-2,4-diamine.

A third invention is directed to a surface treatment method. More specifically, the surface treatment method according to the third invention is a treatment method that uses the compound α. The surface treatment is performed for the purpose of bonding by, for example, the compound α. The surface treatment is performed for the purpose of achieving chemical reaction or physical absorption by, for example, the compound α. The third invention is a method for coating the substrate with, for example, a solution containing the compound α. Examples of the coating method include an immersing method, a spraying method, and a brush coating method. As a matter of course, the coating method is not limited to these examples. An evaporation method may be employed instead of the coating method. According to the method of the third invention, for example, the compound α is evaporated to be sticked to (deposited on) the substrate. Of course, the coating method is simpler than the evaporation method. Also, the coating method is more cost saving than the evaporation method. Preferably, before being coated with the compound α, the substrate is subjected to one or more treatments selected from the following group. Examples of the treatment include cleaning treatment, corona discharge treatment, plasma discharge treatment, ultraviolent ray irradiation, acid treatment, alkaline treatment, steam treatment, and chemical conversion coating. After being coated with the compound α, the substrate is subjected to heating treatment, as required. For example, hydroxides of Group I Element, salts of Group I Element, hydroxides of Group II element, salts of Group II Element, ammonia, ammonium salts, hydrazine, hydrazine derivatives, amines, phosphoric acids, phosphates, carbonates, carboxylic acids, carboxylates, silicic acids, silicates, and fluorides are employed for the chemical conversion coating. For example, a film is formed on a surface of a metal according to the chemical conversion coating.

Treatment of the substrates made of various materials with the compound α (e.g., coating of the surfaces of the substrates with the compound α) ensures obtainment of materials having the identical surface function. As a matter of course, the substrates have different physical properties in bulks, but basically have the identical physical properties in surfaces. Expected surface physical properties of these materials are metal catalyst absorptivity, chemical and physical compound reactivity, metalizing properties, heat resisting properties, corrosion resistance, oxidation resistant properties, UV stability, hydrophobicity, hydrophilicity, soldering adherability, bondability, electroconductivity, colorability, stainability, printability, and transcription ability. Further, when the treatment is performed onto the surfaces of the materials with functional groups such as various sorts of functional compounds and functional group-containing compounds (silane coupling agents) and functionality imparting agents, the materials are capable of obtaining the surfaces having heterologous functionality and containing functional groups. The heterologous functionality is capable of imparting catalytic properties, chemical and physical reactivity, metalizing properties, heat resisting properties, corrosion resistance, oxidation resistant properties, UV stability impartment, hydrophobicity, water repellency, lipophilicity and hydrophilicity, soldering adherability, bondability, stickiness, electric insulation, electroconductivity, antifouling properties, antibacterial activity, surface smoothness and roughness, wear and abrasion resistance, colorability, stainability, printability, transcription ability, decorating properties, biocompatibility, and luminescence and light-selective absorptivity.

In work and assembly in the manufacturing work, the surface properties become more influential. The number of factors demanded in the manufacturing work, e.g., kinds and amounts of parts, number of work processes and work time, and assembly processes and assembly time, becomes larger, resulting in causing the manufacturing work to face to difficulties. It is considered that one of the factors posing the difficulties is a difference in surface properties between parts, i.e., wide variation of surface properties of the parts. To cope with the difficulties, many surface treatment technologies are developed for many kinds of materials. The surface treatment technologies are important to the manufacturing work. However, competition becomes harder due to the change of time. It is impossible for the conventional catch-up technology to catch up with this change of time. It becomes more difficult for the countries having improved technologies to win in the competition. In order to breakthrough the present situation, it becomes material to develop innovative technologies having a concept different from the conventional catch-up technology. Departing from the material dependency of the conventional surface treatment technology, if it is possible to provide an identical surface condition to many materials with the use of the same treatment agent by the same method, the above described problem will be solved significantly. A surface treatment agent (identical surface making-functionalizing agent) capable of imparting such material independency should have three functions such as an "adherence function", a "reactivity function", and a "diversity function" with respect to many kinds of materials such as the metal materials, the ceramic materials, and the high polymerized materials.

An identical surface making-functionalizing film obtained by the identical surface making-functionalizing agent has a constant adhesion strength (shows a cohesive failure) for every kind of material. What is important for the agent is absence of the interfacial debonding with respect to many kinds of materials in a debonding test. In other words, it is material for the agent to show the sufficient adhesion strength and cohesive failure even between the different materials. Further, a reactivity function of the identical surface making-functionalizing agent is utilized for causing the surface to have various different functions. Therefore, the agent needs to take a role of triggering chemical reaction throughout (or to a portion of) the film to cause the portion to have a different function. It is material that the surface of the material to which such function was imparted comes to have a diversity function, i.e., comes to take various roles. It is further important that such diversity function is to be imparted to the surface of the material by a simple method. If a special method is required to realize the above impartment of the function, practical realization thereof will be difficult.

The physical properties of all the materials are shown by the sum of bulk attributes and surface attributes. People engaged in the manufacturing work needs to know these attributes deeply. For example, the surface properties of the materials include many factors such as wettability, stickiness, water repellency, hydrophilicity, adhesive property, absorptivity, smoothness, water-holding property, electrification characteristic, reactivity, and hardness. Understanding of the above factors demands great time and efforts. To avoid these troublesome in the manufacturing work and to realize the smooth manufacturing work, it is important to impart the same condition to the surfaces of the materials. In other words, realization of impartment of the same condition to the surfaces will be convenient for the manufacturing work, i.e., will save time to understand the above described various factors, as well as will be practical. In order to speed up the manufacturing work, homogenization (identification) of the surfaces of the materials is essential. However, a method for homogenizing the surface conditions of many different kinds of materials (the metals, the ceramics, and the organic materials) to a level equal to or more than about 90% is not known yet.

The inventors studied based on this point of view and found that, when the compound α is brought into contact with a surface of a substrate, the compound a reacts with (or tightly adheres to) a material of the substrate. As a result, the surface of the material comes to have, for example, a hydroxylsilyl group (or an alkoxysilyl group) and/or an amino group, and thus characteristics of the substrate is largely modified. Whether or not a surface functionalizing agent (the compound α) reacts with the substrate to be bonded thereto via chemical bonding or whether or not the surface functionalizing agent adheres to the substrate via tight absorptive power becomes apparent from a result of detection, in the XPS analysis, of N and Si as unique elements of the surface functionalizing agent (the compound α). If the surface functionalizing agent (the compound α) is brought into contact with another compound that reacts with (or adsorbs to) the hydroxylsilyl group and/or the amino group, the surface of the substrate is modified to have another function. As described above, it is possible to modify the surface of the substrate to any intended functional surface or useful surface. Thus obtained surface functionalizing material comes to be used in various ways, for example, as an amphipathic material having a reversibly conversed property between hydrophilic property and hydrophobic property, a material for metalizing an organic functional material as a whole or in part, a material for bonding, for example, between organic functional materials and metal materials and between ceramic materials and organic materials by fluid/nonfluid, a material for electroless plating and electroplating of functionalizing metal materials, and a material for protection against corrosion and antioxdation of the surfaces of functionalizing metal materials.

In some cases, the substrate coated with the compound α is considered as a final product. However, in many cases, the substrate coated with the compound α is also considered as an intermediate material to the next step.

Contact between the compound α and the functional group and/or the functional-imparting agent triggers reaction therebetween. As a result of the reaction, a dissimilar functional group-containing material and a heterologous functional surface-containing material can be obtained. Such materials become products owing to the functions of their own or become useful as composite products by bonding, lamination, and assembly of the same kinds of materials and/or different kinds of materials. There are some cases where plating is provided to the materials.

Hereinafter, a detailed description thereof will be given.
[Surface Treatment Agent]

The surface treatment agent of the present invention has an "adherence function", a "reactivity function", and a "diversity function".

More specifically, the surface treatment agent of the present invention is the above described compound α or a compound containing the compound α.

More preferably, the compound α is represented by the General Formula [I]. Further preferably, the compound α is represented by, for example, the General Formula [II] or the General Formula [III]. For example, the compound α is represented by the General Formula [IV] or the General Formula [V]. Examples of the compound α include N,N'-bis(2-aminoethyl)-6-(3-triethoxysilylpropyl)amino-1,3,5-triazine-2,4-diamine;

6-(3-triethoxysilylpropyl)amino-2,4-dihydrazinyl-1,3,5-triazine;

2-(N,N'-di-3-triethoxysilylpropyl)amino-4,6-di(2-aminoethyl)amino-1,3,5-triazine;

2-(2-aminoethyl)amino-4,6-di(3-triethoxysilylpropyl)amino-1,3,5-triazine;

6-(2-aminoethyl)amino-2,4-bis(methylethylketoxyminosilyl)propylamino-1,3,5-triazine;

6-(2-aminoethyl)amino-2,4-di(triisopropoxysilyl)propylamino-1,3,5-triazine;

6-(2-aminoethyl)amino-2,4-di(triacetoxysilyl)propylamino-1,3,5-triazine;

6-(2-aminoethyl)amino-2,4-di(triisopropenoxysilyl)propylamino-1,3,5-triazine;

6-(2-aminoethyl)amino-2,4-di(triisopropoxysilyl)propylamino-1,3,5-triazine;

6-(2-aminoethyl)amino-2,4-di(tribenzoxysilyl)propylamino-1,3,5-triazine;

6-(2-aminoethyl)amino-2,4-bis(triethoxysilylhexyl)amino-1,3,5-triazine;

6-(2-aminoethyl)amino-2,4-bis(triethoxysilyldodecyl)amino-1,3,5-triazine;

2,4-di(2-aminoethyl)amino-6-bis(methylethylketoxyminosilyl)propylamino-1,3,5-triazine;

2,4-di(2-aminoethyl)amino-6-bis(methylethylketoxyminosilyl)propylamino-1,3,5-triazine;

2,4-di(2-aminoethyl)amino-6-di(triisopropoxysilyl)propylamino-1,3,5-triazine;

2,4-di(2-aminoethyl)amino-6-di(triacetoxysilyl)propylamino-1,3,5-triazine;

2,4-di(2-aminoethyl)amino-6-di(triisopropenoxysilyl)propylamino-1,3,5-triazine;

2,4-di(2-aminoethyl)amino-6-di(triisopropoxysilyl)propylamino-1,3,5-triazine;

2,4-di(2-aminoethyl)amino-6-di(tribenzoxysilyl)propylamino-1,3,5-triazine;

2,4-di(2-aminoethyl)amino-6-bis(triethoxysilylhexylamino)-1,3,5-triazine;

2,4-di(2-aminoethyl)amino-6-bis(triethoxysilylpropyl)amino-1,3,5-triazine;

N,N'-bis(2-dimethylaminoethyl)-6-(3-triethoxysilylpropyl)amino-1,3,5-triazine-2,4-diamine;

N,N'-bis(2-aminohexyl)-6-(3-triethoxysilylpropyl)amino-1,3,5-triazine-2,4-diamine;

N,N'-bis{2-[bis-(2-aminoethyl)amino-]ethyl}-6-(3-triethoxysilylpropyl)amino-1,3,5-triazine-2,4-diamine; and N,N'-bis(12-aminododecyl)-6-(3-triethoxysilylpropyl)amino-1,3,5-triazine-2,4-diaminine.

The compound is synthesized from, for example, [Reaction Formula 1] or [Reaction Formula 2].

REACTION FORMULA 1

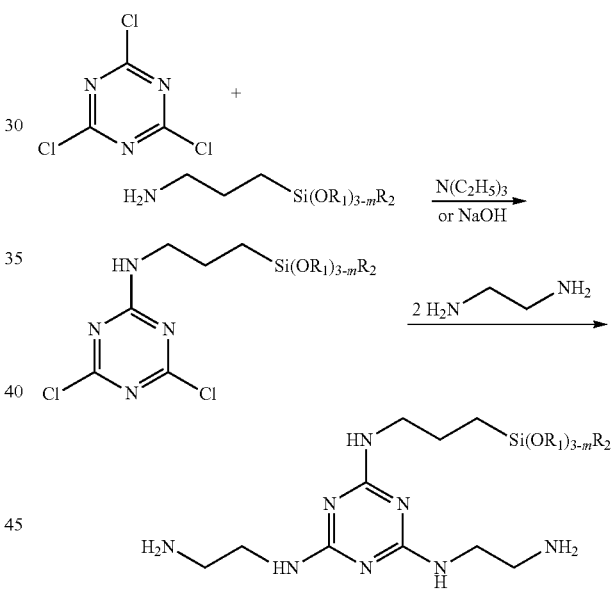

REACTION FORMULA 2

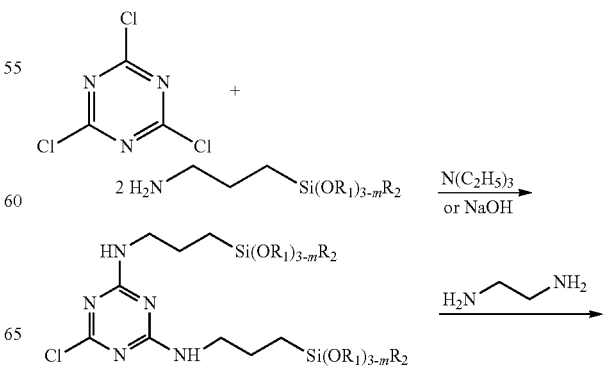

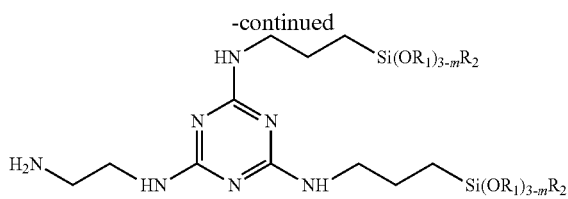

The solvent to be used in the reaction is essentially required not to react with the amino group, the alkoxysilyl group, and the functional group contained in the alkoxysilyl group. A solvent that satisfies the above condition differs according to a combination of the amino group and the functional group containing-alkoxysilyl group. Therefore, it is difficult to uniquely decide the solvent. However, just for the reference sake, listed as examples of the solvent are water, alcohols (e.g., methanol, ethanol, isopropanol, ethylene glycol, propylene glycol, cellosolve, and carbitol), ketones (e.g., acetone, methyl ethyl ketone, and cyclohexanone), aromatic hydrocarbons (e.g., benzene, toluene, and xylene), aliphatic hydrocarbons (e.g., hexane, octane, decane, dodecane, and octadecane), esters (e.g., ethyl acetate, methyl propionate, and methyl phthalate), ethers (e.g., tetrahydrofuran, ethyl butyl ether, and anisole), and mixtures thereof.

In the reaction, a reaction temperature is governed by activity between the triazine compound as the skeletal formula and the amino group (e.g., primary diamine or primary triamine) and the functional group of the alkoxysilyl group-containing compound. Therefore, the reaction temperature is not uniquely decided. However, for the sake of information, the reaction temperature is within about a range between −20° C. and 200° C. Preferably, the reaction temperature is within a range between −10° C. and 100° C. The solvent reacts slowly at a temperature lower than −20° C., resulting in lowering the productivity. The temperature higher than 200° C. necessitates additional equipment such as an autoclave in many cases. Also, the solvent reacts excessively quickly at a temperature higher than 200° C. As a result, a secondary product tends to be generated. Accordingly, a preferable temperature is what exemplified above.

What is important is that a ratio (molar ratio) of an amino compound (a primary diamine and a primary triamine) to one carbon element of the triazine compound as the skeletal formula (the former/the latter) is equal to or more than 1. Generally, the ratio is a value within a range between 2 and 10. If the ratio is less than 1, there are a case that a target product is hardly obtained and a case that a raw material is left. If the ratio becomes larger, e.g., beyond 10, generation of impurities decreases; however, removal of unreacted amine takes time. This invites lowering of production efficiency. Next, what is important is that a ratio (molar ratio) of the alkoxysilyl group-containing compound to one carbon element of the triazine compound as the skeletal formula (the former/the latter) is also equal to or more than 1. Generally, the ratio is a value within a range between 1.05 and 1.50. If the ratio is less than 1, unreacted material is left. This invites lowering of a yield of amount. If the ratio becomes beyond 1.50, generation of impurities increases. This invites lowering of production efficiency.

Even in a case where the compound α is a mixture of two or more different materials, the treatment is effective. Therefore, the reaction product can be used as it is without necessity of isolation to a single compound. Here, the mainly obtainable compound is a monomer represented by the compound α. In addition thereto, byproducts are obtainable in the course of the chemical compounding process, i.e., a condensation product constituted of a dimer resulting from reaction between a triazine having an amino group at its terminal and a triazine having an unreacted carbon atom, oligomer, and an alkoxysilyl group and/or a mixture thereof are obtainable.

Thus obtained compound α (the compound represented by General Formula [I]) is provided on the substrate by a coating means. For example, in a case where the compound α (the compound represented by General Formula [I]) is not liquid, the compound α is added into the solvent. Then, the substrate is immersed into the solvent to be coated with the compound α. Spraying of the solution also ensures coating of the compound α on the substrate. The spin coat method is also employable. The brush coating method is also employable. Various coating methods are employable in addition to the above described methods. In addition to the coating methods, a method in which the compound α is evaporated to be deposited onto the substrate is also employable. In any way, it is possible to carry out the coating method simply and easily. Further, the compound α tightly adheres to the substrate even via the coating method. Alternatively, the compound α is bonded to the substrate via the chemical reaction. That is, only contact of the compound α with the substrate establishes tight adherence therebetween. Therefore, an effect of the identical surface making-function is produced.

An average film thickness of the compound α is within about a range between 1 nm and 20 nm. In a case where the compound α is chemically bonded to the substrate, the film thickness of the compound α becomes thinner than the above range. In a case where a strong adhesive force is obtained by a method other than the chemical bonding, the film thickness of the compound α becomes relatively thick. The relatively thick means only a level thicker than the thickness in the case of the chemical bonding. In a case where the compound α is bonded to the surface of the substrate via the chemical reaction, an average film thickness is within about a range between 1 and 5 nm. In a case where the compound α is bonded to the substrate by a strong absorption force, the average film thickness becomes thicker than the above described thickness (about a range between 1 and 5 nm). The strong adhesive force is generated in a case where vaporization of the compound α does not occur even when the compound α is left for a long time under super high vacuum condition of a level of $10^{-6}$ Pa. Under such condition, an XPS analysis is employable. Meanwhile, the above mentioned adhesion strength is a level at which a silicone rubber phase is broken out at a time when the silicon rubber is bonded to the surface of the substrate. It is said that such power corresponds to the power of the chemical bonding. Such adhesive force is a force of a level inconsiderably stronger than an adhesive force between molecules.

The solvent employed in coating may be identical to the solvent to be employed in the reaction. More specifically, the solvent may be water, alcohol, ketone, aromatic hydrocarbons, aliphatic hydrocarbons, esters, ethers, and mixtures thereof. A concentration of the compound α is within about a range between 0.001 wt % and 10 wt %. With the concentration less than 0.001 wt %, i.e., when the concentration is too weak, only a poor effect is produced. With the concentration exceeding 10 wt %, i.e., when the concentration is too strong, complicated post-treatment is required. A temperature during the coating treatment is about a range between −20° C. and 200° C. A time required for the coating treatment is about a range between 0.1 sec. and 12 hrs. The concentration of the compound α, the treatment temperature, and the treatment time relate to one another. An optimum solution thereof can be obtained via repetition of tests.

After the compound α is provided on the substrate via the coating method or the evaporation (deposition) method, the post-treatment substrate is left at a temperature within a range between −20° C. (preferably, equal to or greater than 15° C.) and 200° C. under vacuum atmosphere, under ordinary atmosphere, or under pressure. The leaving time is 0.1 sec. to 12 hrs. This is considered as fixing treatment for causing the compound α to be fixed onto the substrate.

When the film of the compound α chemically reacts, the film of the compound a comes to contain the acid amide group (—CONH—), the amino group ($NH_2$—, —NH—), the alkoxysilyl group (—SiOR), and/or the hydroxysilyl group (—SiOH). When the film of the compound α is generated to be tightly adhered to the substrate, the compound a comes to contain the amino group ($NH_2$—, —NH—), the alkoxysilyl group (—SiOR), and/or the hydroxysilyl group (—SiOH). In the water or in the solution, the alkoxysilyl group is hydrolyzed to be modified to a hydroxysilyl group. The alkoxysilyl group is hydrolyzed in moisture to be modified to the hydroxysilyl group. A hydrogen bonding (H . . . N . . . H) and/or a salt linkage ($>NH_2^-$ . . . $^+OSi<$) are formed between the amino group ($NH_2$—, —NH—), a localized electron nitrogen of the triazine ring, and the hydroxysilyl group. It is considered that this causes the surfaces of the substrates to be substantially the same. In other words, the film of the compound α facilitates the identical surface making-functionalizing function.

The film of the compound α is tightly bonded to many kinds of materials (e.g., resin materials such as an olefin resin, a nylon resin, and a polyvinyl alcohol; ceramic materials such as a glass and almina; and metal materials such as Cu and Al). The bonding force is unconsiderably stronger than the primary bond and the secondary bond. On the assumption of an atomic state of a nitrogen atom in the XPS analysis, flowing of electrons into the nitrogen atom was confirmed. It is considered that a state of excess of electrons of the nitrogen atom induces the London dispersion force to cause the compound α to tightly adhere to the olefin resin. It is considered that the characteristics of the identical surface making-functionalizing film results from the stabilization caused by interactions between sides of the film and a bottom of the film. In general materials, a film is formed with a balanced intermolecular force in every direction. However, in the identical surface making-functionalizing film, the bonding force in a lateral direction is stronger than the bonding force in a vertical direction.

The film of the compound α that is bonded to the surface of the substrate by reaction or absorption contains the amino group, the alkoxysilyl group, and/or the hydroxysilyl group in its surface. This means that the surface of the film of the compound α contains the reactivity functional group. The reactivity functional group is used to impart the more reactivity and functionality.

[Function-imparting Agent and Reactivity-imparting Agent]

The surface of the film made of the compound α contains the amino group, the alkoxysilyl group, and/or the hydroxysilyl group therein. These functional groups have the reactivity. Therefore, the compound α is capable of reacting with various types of substances (reagents). For example, the reaction occurs among a homogeneousness functional reagent, a heterogenous functional reagent, and a nanoparticle dispersion reagent. The surface treatment by the substance (reagent) modifies the surface to a material having a large variety of functions.

The homogeneousness functional reagent contains two or more identical functional groups. The homogeneousness functional reagent contains, for example, di(hydroxyphenyl) methane, di(2,4-hydroxymethyl)phenol, di(2,4-hydroxymethyl)-3,5-xylenol, di(2,4-dihydroxymethyl)-m-cresol, melamine, trimethylolmelamine, hexamethylolmelamine, trimethoxymethylmelamine, hexamethoxymethylmelamine, guanamine, tetramethylurea, cyanuric acid, phthalic acid, terephthalic acid, succinic acid, adipic acid, sebacic acid, trimellitic acid, pyromellitic acid, rosin succinic acid, phthalic anhydride, trimellitic anhydride, rosin maleic anhydride, pyromellitic acid anhydride, dihydroxy dimethyl silicon, trihydroxy methyl silicon, octandithiol, pentaerythritol tetrathioglycolate, 1,4-dimercaptobenzene, 1,3,5-trimercaptobenzene, 1,5-dimercaptonaphthalene, 2,4,6-trithiol-1,3,5-triazine, 2,4-dithiol-6-(dibutylamino)-1,3,5-triazine, 2,4-dithiol-6-anilino-1,3,5-triazine, 2,4-dithiol-6-(N-phenyl)amino-anilino-1,3,5-triazine, 2,4-dithiol-6-(N-phenyl)amino-isopropylaniline-1,3,5-triazine, 2,4-dithiol-6-(N-phenyl)amino-phenoxy-1,3,5-triazine; 2,4-dithiol-6-(N-allyl-2-perfluorooctyl)ethylaminophenoxy-1,3,5-triazine, perfluorooctanoylchloride, perfluorodecanoic acid, perfluoroazelique acid, 3-(1H,1H,7H-dodecane fluoroheptyloxy)-1,2-epoxypropane, 1,3,5-phenylaminobenzene, 1,3-naphtylaminobenzene, 1,5-diaminonaphthalene, bis-3-(N,N-dimethylaminophenyl)amine, tris(4-aminophenyl)amine, bis(4-aminophenyl)amine, N-phenyl-2,4-anilinoamine, bis(1,4-phenylamino)benzene, hexamethylene diisocyanate, toluoylene diisocyanate, triisocyanate phenylmethane, dicyclohexyldimethylmethane, p,p'-diisocyanate, hexamethylene dimethylcarbamate, toluoylenediethylcarbamate, 2,2'-bis(4-glycidylphenyl)propane, diglycidyloctane, tetraglycidylaminodiphenylmethane, diglycidylethers, divinylbenzenedioxide, and 2,6-diglycidyl phenyl glycidyl ethers.

Examples of the heterogenous functional reagent include 6-alkoxysilylpropylamino-1,3,5-triazine-2,4-dithiol monosodium, 6-bis(3-alkoxysilylpropyl)amino-1,3,5-triazine-2,4-dithiol monosodium, 6-N-cyclohexyl-N-(3-(triethoxysilyl)propylamino)-1,3,5-triazine-2,4-dithiol monosodium, vinylmethoxy siloxane homopolymer, bis(triethoxysilylpropyl)tetrasulfide, 3-mercaptopropyl trimethoxysilane, 3-aminopropyl triethoxysilane, 2,4-bis(2-aminoethylamino)-6-(3-triethoxysilylpropylamino)-1,3,5-triazine, 2,4-dihydrazino-6-(3-triethoxysilylpropylamino)-1,3,5-triazine, 6-alkoxysilylpropylamino-1,3,5-triazine-2,4-dithiol, 6-alkoxysilylpropylamine, 6-bis(3-alkoxysilylpropyl)amine, 6-N-cyclohexyl-N-(3-(triethoxysilyl)propylamine), vinylmethoxy siloxane homopolymer, bis(triethoxysilylpropyl)tetrasulfide, 3-mercaptopropyl trimethoxysilane, 3-aminopropyl triethoxysilane, (3-acryloxypropyl)trimethoxysilane, methacryloxypropyl trimethoxysilane, triethoxysilyl undecanal, 4-aminobutyl triethoxysilane, m-aminophenyl triethoxysilane, 11-aminoundecyl trimethoxysilane, N-(3-triethoxysilylpropyl)pyrrole, N-(2-aminoethyl)-3-aminopropyltrimethoxysilane, (3-aminopropyl)methyldiethoxysilane, aminopropylsilanetriol, N-(2-aminoethyl)-3-aminopropylsilanetriol, N-methylaminopropyl trimethoxysilane, N-butylaminopropyl trimethoxysilane, N-trimethoxysilylpropyl trimethyl ammonium chloride, bis(trimethoxysilylpropyl)amine, 3-(triethoxysilyl)propyl succinic anhydride, 6-azide sulfonylhexyl triethoxysilane, 2-(4-chlorosulfonyl)ethyltriethoxysilane, 2-(3,4-epoxycyclohexyl)trimethoxysilane, (3-glycidioxypropyl)trimethoxysilane, 10-(carbomethoxy) decyl dimethyl methoxysilane, 3-chloropropyl trimethoxysilane, 7-bromoheptyl trimethoxysilane, 3-isocyanatopropyl triethoxysilane, (3-triethoxysilyl)-t-butylcarbamate, 2-(diphenylphosphino)ethyl triethoxysilane, diethylphosphate ethyltriethoxysilane, 3-mercaptopropyl trimethoxysilane, 5-(bicycloheptinyl)triethoxysilane, (3-cyclopentadiene-propyl)triethoxysilane, 2,4-dithiol-6-(triethoxysilylpropyl)amino-1,3,5-triazine, 2,4-dithiol-6-triethoxysilylpropylthio-1,3,5-triazine, 2-thiol-4,6-di(N,N'-triethoxysilylpropyl)amino-1,3,5-triazine, 2-thiol-4,6-di(triethoxysilylpropylthio)-1,3,5-triazine, 2,4-diazido-6-(triethoxysilylpropyl)amino-1,3,5-triazine, 2-azido-4,6-di(N,N'-triethoxysilylpropyl)amino-1,3,5-triazine, hexadecafluorododeca-11-enyl-1-trimethoxysilane, [tris(tridecafluoro-1,1,2,2-tetrahydrooctyl)dimethylsiloxane]chlorosilane, and tridecafluoro-1,1,2,2-tetrahydrooctyltrimethoxysilane.

Examples of the nanoparticle dispersion reagent include an organism-related nanoparticle dispersion reagent such as protein and enzyme having a particle diameter of a range between 1 nm and 100 nm, a polymer nanoparticle (monodispersed polymer nanoparticle or polydispersed polymer nanoparticle) dispersed reagent, a metal nanoparticle dispersion reagent, a metallic oxide nanoparticle dispersion reagent, a metal inorganic salt nanoparticle dispersion reagent, and a metal nanoparticle dispersion reagent. They are produced by a gas phase method (e.g., a chemical reaction method, a thermal CVD method, a prasma CVD method, a molecular beam epitaxy, an evaporation to concentration method, a sputtering method, an EB heating method, a gas evaporation method, a pulsed laser ablation method, and a resistive heating), a liquid-phase method (e.g., a chemical liquid-phase method, a chemical reaction sedimentation method, a microwave heating method, a reverse micelle method, a normal micelle method, a hydrothermal method, a sol-gel method, a physical liquid-phase method, and a spray-drying technique), and a solid phase method (e.g., a baking method and a heating furnace method). Examples of the metal nanoparticles include nanoparticles of, for example, Fe, Co, Ni, Au, Ag, Cu, Sn, Pb, Ge, In, Pt, and Zn. Examples of the metallic oxide nanoparticles include nanoparticles of $Fe_3O_4$, $CeO_2$, $BaTiO_3$, $PbSrTiO_3$, $CaPt_{0.05}Ti_{0.95}O_3$, $Al_2O_3$, MgO, $Mn_3O_4$, NiO, $SiO_2$, $TiO_2$, $ZrO_2$, $YO_3$—$ZnO_2$, and clay. Examples of the metal inorganic salt nanoparticles include nanoparticles of AgCl, AgBr, a tin compound (e.g., stannous formic acid, stannous acetic acid, stannous propionic acid, stannous butyric acid, stannous valeric acid, stannous caproic acid, stannous caprilic acid, stannous capric acid, stannous lauric acid, stannous benzoic acid, stannous maleic acid, stannous fumaric acid, stannous methoxy, stannous ethoxy, stannous propoxy, stannous butoxy, stannous pentoxy, stannous hexoxy, stannous phenoxy, and stannous benzyloxy). Examples of the organism-related nanoparticles include nanoparticles of protein, bacteria, virus, DNA, antibody, enzyme, and hormone. Examples of the polymer nanoparticles include nanoparticles of polyethylene, polymethylmethacrylate, polyethylmethacrylate, polybutylmethacrylate, ethylpolyacrylate, hexylpolyacrylate, polyacrylic acid amide, polydimethylacrylic acid amino, polyisopropylacrylic acid amide, and polyvinyl acetate. In addition to the above, nanoparticles of, for example, fullerene, carbon nanotube, carbon black, ZnS, and PbSe are also exemplified.

When each of the agents (function-imparting agents and/or reactivity-imparting agents) is brought into contact with the compound α that was bonded to the surface of the substrate, the material thereof is modified to have various functions. Such contact is achieved by a proper means selected from the coating method, the deposition method, and the sputtering method. The solvent to be used for coating can be the same one used in coating the compound α. It is possible to apply the technological concept employed in coating the compound α to the concentration, the treatment time, the treatment temperature, and the post-treatment. A film thickness of the agent (function-imparting agent and/or reactivity-imparting agent) is set as required. The compound α and the agent (function-imparting agent and/or reactivity-imparting agent) are bonded to each other via an adhesive force caused by, for example, chemical bonding, ion bonding, hydrogen bonding, Van der Waals force, or London dispersion force.

[Substrate]

Examples of the substrate targeted in the present invention include substrates made of various materials. Examples of the materials include the metal materials, the ceramic materials, the organic high polymerized materials, and the inorganic high polymerized materials. Alternative examples thereof include composite materials made of mixtures of the above materials. The substrate may be formed into any shape. For example, the substrate may be formed into various shapes such as a plate, a rod, a post, a ball, a semisphere, a frame, a fiber, a string, powders, nonwoven fabric, fabric, net, foam, a film, a sheet, and a laminated body.

Examples of the metal material include various metals, alloys, shape memory alloys, super-elastic alloys, functional metals, amorphous metals, and fiber-reinforced metal blocks. Examples of structural elements of the metal material include Be, Mg, Ca, Sr, Ba, Ra, Sc, Y, Ti, Zr, V, Nb, Ta, Cr, Mo, W, Mn, Fe, Co, Rh, Ir, Ni, Pd, Pt, Cu, Ag, Au, Zn, Cd, Hg, Al, Ge, Sn, Pb, Sb, Bi, and Nd. Examples of the alloys include iron alloys (steel, carbon steel, and cast iron), copper alloys (phosphor bronze, brass, cupronickel, beryllium copper, and copper-titanium alloy), aluminum alloys (The alloy content is/are selected from the group consisting of Cu, Mn, Zn, Ni, and the like, as required, in addition to Al), magnesium alloys (alloy content is/are selected from the group consisting of Zn, Ca, and the like, as required, in addition to Mg), a zinc alloy, a tin alloy, a nickel alloy, a gold alloy, a silver alloy, a platinum alloy, a palladium alloy, a lead alloy, titanium alloys (α type alloy, β type alloy, and α+β type alloy), a cadmium alloy, a zirconium alloy, a cobalt alloy, a chromium alloy, a molybdenum alloy, a tungsten alloy, a manganese alloy, ferritic stainless steel, martensitic stainless steel, austenitic stainless steel, precipitation-hardened stainless steel, a nickel-titanium alloy, an iron-manganese-titanium alloy, and a super-elastic alloy (nickel-titanium alloy). This, however, should not be construed in a limiting sense.

Preferably, the metal materials are subjected to cleaning treatment to clean up the surface thereof prior to the treatment with the compound α. Examples of the cleaning treatment include wet cleaning (aquaous base: pure water, tap-water, and function water; nonaquaous base: hydrocarbon base and nonflammable solvent base) and dry cleaning (using ultraviolet rays, ozone, combination of ultraviolet rays and ozone, prasma, corona discharge, argonaerosol, and liquefied carbon dioxide).

Examples of the ceramic materials include porcelain (e.g., kaolin, potter's clay, pottery stone, feldspar, silica, quartz, and almina), glass, cement, plaster, and enamel. In view of the composition, oxide-based materials, zirconia-based materials, hydroxide-based materials, carbide-based materials, carbonate-based materials, nitride-based materials, halide-based materials, and phosphate-based materials are exemplified. More specifically, barium titanate, $Bi_2Sr_2Ca_2Cu_3O_{10}$, high temperature superconductive ceramics, boron nitride, ferrite, lead zirconate titanate, silicon carbide, silicon nitride, steatite, zinc oxide, alumina nitride, forsterite, cordierite, sialon, machinable ceramics, zircon, barium titanate, lead zirconate titanate, mullite, carbon black, white carbon, silica-based diatomite, fired diatomaceous earth, quartz/silica, cristobalite, kaolinite, kaolin clay, fired clay, talc, potassium mica, sericite, wollastonite, serpentine, pyrophyllite, calcium carbonate, barites, titanium oxide, magnesium basic carbonate, dolomite, and aluminum oxide are also listed as specific examples of the ceramic materials. This, however, should not be construed in a limiting sense.

Preferably, the ceramic materials are also subjected to cleaning treatment for cleaning the surfaces thereof prior to the treatment with the compound α. For example, the ceramic materials are subjected to the wet cleaning or the dry cleaning.

The typical organic high polymerized material includes C—C bonding and/or C—H bonding. Examples of the organic high polymerized material include heat-curable resin, thermoplastic resin, fiber reinforced plastic, photo-curing resin, vulcanized rubber, and un-crosslinked rubber. The skeletal formula of the high polymer molecule is formed into a two-dimensional linear structure or a three-dimensional net structure. Examples of the polymer having the two-dimensional linear structure include cellulose such as hydroxyethyl cellulose, cellulose ester (derivatives) such as cellulose diacetate, starch, polyvinyl acetate resin, low-density polyethylene, high-density polyethylene, polypropylene, ethylene-propylene copolymer, petroleum resin, polystyrene, syndiotactic-polystyrene, styrene copolymer, chroman-indene resin, terpene resin, styrene-divinyl benzen copolymer, acrylnitrile-butadiene-styrene copolymer (ABS) resin, polymethyl acrylate, polyethyl acrylate, polyacryl nitrile, polymethyl acrylate, polymethyl methacrylate, polyethyl methacrylate, polycyano acrylate, polyvinyl acetate, ethylene-vinyl acetate copolymer (EVA) resin, polyvinyl alcohol, polyvinyl formal, polyvinyl acetal, vinyl acetate copolymer, polyvinyl chloride, vinyl chloride-vinyl acetate copolymer, vinyl chloride-ethylene copolymer, poly(vinyliden fluoride), vinyliden fluoride-ethylene copolymer, vinyliden fluoride-propylene copolymer, 1,4-transpolybutadiene, 1,2-transpolybutadiene, polyoxy methylene, polyethylene glycol, polypropylene glycol, phenol-formalin resin, cresol-formalin resin, resorcinol resin, melamine resin, xylene resin, toluene resin, glyptal resin, modified glyptal resin, polyethylene terephthalate (PET), polybutylene terephthalate (PBT), unsaturated polyester resin, polyester acrylate, allylester resin, polycarbonate (PC), 6-nylon, 6',6-nylon, 6',10-nylon, polyimide (PI), poly(p-phenylenepyromellitimide), poly(p-phenylenebiphenyl-3,4,3',4'-tetracaboximide), poly(p-phenyleneoxydiphthalicimide), polyp-phenylenebenzophenone-3,4,3',4'-tetracaboximide), poly(p-phenylendiphenylsulfone-3,4,3',4'-tetracaboximide), poly(p-phenylencyclobutane-1,2,3,5-tetracaboximide), Kaptons, polyamide, polybenzimidazole, polyamideimide, silicon resin, addition-curable type silicone rubber, polymerization-curable type silicone rubber (polysiloxane containing vinyl group in side chain, polysiloxane containing vinyl group at both terminals), condensation-curable type silicone rubber, addition-curable type silicone resin, furan resin, polyurethane resin, epoxy resin (EP), polyphenylene oxide, polydimethylphenylene oxide, a polymer alloy made of polyphenylene oxide (or polydimethylphenylene oxide) and triallylisocyanurate, a polymer alloy made of polyphenylene oxide (or polydimethylphenylene oxide), triallylisocyanurate, and peroxide, polyxylene, polyphenylene sulfide (PPS), polycycloolefin (COP), polysulfone (PSF), polyethersulfone (PES), polyetheretherketone (PEEK), liquid crystal resin (LCP), polyurethane (U), natural rubber, 1,4-cisbutadiene rubber, isoprene rubber, polychloroprene, styrene-butadiene copolymer rubber (SBR), hydrogenated styrene-butadiene copolymer rubber, acrylnitrile-butadiene copolymer rubber (NBR), hydrogenated acrylnitrile-butadiene copolymer rubber, polybutene rubber, polyisobutylene rubber, ethylene-propylene rubber (EPR), ethylene-propylene-diene rubber (EPDM), ethylene oxides-epichlorohydrin copolymer rubber, chlorinated polyethylene rubber, chlorosulfonated polyethylene rubber, alkylated chlorosulfonated polyethylene rubber, chloroprene rubber, chlorinated acryl rubber, brominated acryl rubber, flourine rubber (FKM), epichlorohydrin and epichlorohydrin copolymer rubber, chlorinated ethylene-propylene rubber, chlorinated buthyl rubber, brominated buthyl rubber, tetra-fluoro ethylene, homopolymer ruber such as hexafluoropropylene, vinylidene fluoride, and tetrafluoroethylene, and copolymer rubber and terpolymer rubber thereof, ethylene-tetrafluoroethylene copolymer rubber, propylene-tetrafluoroethylene copolymer rubber, ethyleneacryl rubber, peroxide type silicone rubber, addition type silicone rubber, condensation type silicone rubber, epoxy rubber, urethane rubber (UR), and elastomers having unsaturated groups at both terminals. The high polymerized material includes, in many cases, some of additives of, for example, crosslinking agents, crosslinking accelerators, crosslinking assistants, radical initiators, cation initiators, photopolymerization initiators, scorch retarders, stabilizers, antioxidants, ultraviolet ray inhibitors, fillers, reinforcers, plasticizers, softeners, colorants, and viscosity modifiers. The polymer having the three-dimensional net structure is obtainable by crosslinking a compound, that was obtained by adding crosslinking agents (and further, as required, crosslinking accelerators and crosslinking assistants) to the two-dimensional linear polymers, under heating and/or lighting environment (polymer containing-crosslinking type high polymer). As a matter of course, the polymer having the three-dimensional net structure is obtainable by polymerizing a compound, that was obtained by adding crosslinking agents (and further, as required, crosslinking accelerators and/or crosslinking assistants) to monomers, under heating and/or lighting environment (monomer containing-crosslinking type high polymer). The monomers in the monomer containing-crosslinking type high polymer is a polymerizable monomer such as a vinyl group, an acrylate group, a methacrylate group, an epoxy group, an isocyanate group, and an oxetane group. Examples of the monomers include a urethane acrylate-based monomer, an epoxy acrylate-based monomer, an ester acrylate-based monomer, an acrylate-based monomer, an epoxy-based monomer, and a vinyl ether-based monomer. More specifically, acrylates are exemplified. Examples of the acrylates include n-alkyl acrylate, i-propyl acrylate, i-butyl acrylate, t-butyl acrylate, cyclohexyl acrylate, β-hydroxyethyl acrylate, diethylene glycol acrylate, polyethylene glycol acrylate, β-hydroxypropyl acrylate, glycidyl acrylate, ethylene glycol diacrylate, diethylene glycol diacrylate, triethylene glycol diacrylate, polyethylene glycol diacrylate, dialkylamino ethyl acrylate, 2-cyanoethyl acrylate, β-ethoxyethyl acrylate, aryl acrylate, benzoyloxyethyl acrylate, benzyl acrylate, phenoxyethyl acrylate, phenoxydiethylene glycol acrylate, 2-hydroxy-3-phenoxypropyl acrylate, tetrahydrofurfuryl acrylate, addition product acrylates of tetrahydrofurfuryl alcohol and ε-caprolactone, bornyl acrylate, dicyclopentenyloxyethyl acrylate, 1,4-butanediol diacrylate, 1,6-hexanediol diacrylate, 1,9-nonandiol diacrylate, neopentyl glycol diacrylate, triethylene glycol diacrylate, tetraethylene glycol diacrylate, polyethylene glycol diacrylate, tripropylene glycol diacrylate, hydroxypivalic acid neopentyl glycol diacrylate, acetal glycol diacrylate, addition product diacrylate of hydroxypivalic acid neopentyl glycol and c-caprolactone, trimethylolpropane triacrylate, trimethylolpropane polyethoxylate triacrylate, trimethylolpropane polyproxylate triacrylate, pentaerythritol triacrylate, dipentaerythritol hexaacrylate, addition product of dipentaerythritol and c-caprolactone, hexaacrylates,acryloxyethyl phosphate, fluoroalkyl acrylate, sulfopropyl acrylate, ethylene glycol diacrylate, propylene glycol diacrylate, polyethylene glycol diacrylate, 1,4-butanediol diacrylate, 1,6-hexanediol diacrylate, trimethylolpropane triacrylate, pentaerythritol tetraacrylate, epoxy (meth)acrylate obtained by addition reaction with acrylic acid, polyurethaneacrylate obtained by reacting 2-hydroxyethylacrylate, diol, and diisocyanate, polyesteracrylate obtained by reacting acrylic acid, polycarboxylic acid, and polyol, urethane acrylate, epoxy acrylate, polyether acrylate, and polyol acrylate. Methacrylates are also exemplified. Examples of the methacrylates include methyl methacrylate, ethyl methacrylate, propyl methacrylate, i-propyl methacrylate, butyl methacrylate, isobutyl methacrylate, sec-butyl methacrylate, t-butyl methacrylate, hexyl methacrylate, octyl methacrylate, i-octyl methacrylate, 2-ethylhexyl methacrylate, decyl methacrylate, lauryl methacrylate, stearyl methacrylate, 2-hydroxyethyl methacrylate, 2-hydroxypropyl methacrylate, 2-dimethylamino ethyl methacrylate, 2-diethylamino ethyl methacrylate, 2-t-butylamino ethyl methacrylate, glycidyl methacrylate, allyl methacrylate, cyclohexyl methacrylate, phenyl methacrylate, nonylphenyl methacrylate, benzyl methacrylate, dicyclopentenyl methacrylate, bornyl methacrylate, 1,4-butanediol dimethacrylate, 1,3-butanediol dimethacrylate, ethylene glycol dimethacrylate, diethylene glycol dimethacrylate, triethylene glycol dimethacrylate, tetraethylene glycol dimethacrylate, polyethylene glycol dimethacrylate, neopentyl glycol dimethacrylate, 1,6-hexanediol dimethacrylate, dipropylene glycol dimethacrylate, trimethylolpropane trimethacrylate, glycerol methacrylate, ethylene glycol dimethacrylate, propylene glycol dimethacrylate, polyethylene glycol dimethacrylate, 1,4-butanediol dimethacrylate, 1,6-hexanediol dimethacrylate, trimethylolpropane trimethacrylate, pentaerythritol tetramethacrylate, epoxy methacrylate obtained by addition reaction with methacrylic acid, polyurethane methacrylate obtained by reaction between 2-hydroxyethyl methacrylate, diol, and diisocyanate, polyester methacrylate obtained by reaction between methacrylic acid, polycarboxylic acid, and polyol, polyether methacrylate, and polyol methacrylate. In addition, examples of the methacrylates further include methacryloxyethyl phosphate, bis.methacryloxyethyl phosphate, arone oxetane, di[1-ethyl(3-oxetanyl)] methylether, 3-ethyl-3-(hexyloxymethyl) oxetane, xylylene dioxetane, phenyl oxetane, oxetanyl silsesquioxane, 3-ethyl-3-(heptyloxymethyl) oxetane, 3-ethyl-3-(2-ethyl hexyloxymethyl) oxetane, 3-ethyl-3-(octyloxymethyl) oxetane, 3-ethyl-3-(dodecyloxymethyl) oxetane, bisphenol A type epoxy monomer, bisphenol F type epoxy monomer, novolac-type epoxy monomer, and toluene diisocyanate. As a matter of course, this should not be construed in a limiting sense. Various types are used for the aforementioned polymerization initiator, crosslinking agent, crosslinking accelerator, and crosslinking assistant. Examples thereof include peroxides, cation polymerization initiators, photoinitiators, sulfur, sulfur-based crosslinking accelerators, polyol-based crosslinking agents, polyamine-based crosslinking agents, polythiol-based crosslinking agents, acrylate-based crosslinking assistants, methacrylate-based crosslinking assistants, and allyl-based crosslinking assistants. Specifically, examples thereof include azobisbutyronitrile, benzo phenon, Michler's ketone, benzoin isopropyl ether, chlorothioxanthone, isopropylthioxanthone, benzyldimethyl ketal, acetophenonediethyl ketal, α-hydroxycyclohexyl phenylketone, and 2-hydroxy-2-methyl-phenylpropane. Further examples thereof include acetophenone derivatives, e.g., 4-(2-hydroxyethoxy)phenyl(2-hydroxy-2-propyl)ketone, α-hydroxy-α,α'-dimethylacetophenone, methoxyacetophenone, and 2,2-dimethoxy-2-phenylacetophenone. Still further examples thereof include benzoin ether-based compounds, e.g., benzoin ethyl ether and benzoin proply ether. Still further examples thereof include ketal derivative compounds such as benzyldimethyl ketal. Still further examples include halogenated ketone, acylphosphine oxide, acylphosphonate, bis(2,6-dimethoxybenzoyl)-2,4,4-trimethylpentyl phosphine oxide, phenyl dimethyl sulfonium chloride, triaryl sulfonium hexafluoro phosphate, triazinedithiol-based crosslinking agent, resin crosslinking agent, polyol crosslinking agent, H-terminal siloxane-based crosslinking agent, and silanol condensation type crosslinking agent. Still further examples thereof include dibenzothiazoyl disulfide, 4-morpholino dithio benzothiazole, N-cyclohexyl-2-benzothiazoyl sulfenamide, N-t-butyl-2-benzothiazoyl sulfenamide, N-oxydiethylene-2-benzothiazoyl sulfenamide, N-diisopropyl-2-benzothiazoyl sulfonamide, N-dicyclohexyl-2-benzothiazoyl sulfenamide, tetramethyl thiuram disulfide, tetraethyl thiuram disulfide, tetrabutyl thiuram disulfide, tetraoctyl thiuram disulfide, amines, hexamethylene tetramine, saligen, quaternary ammonium salts, phosphonium salts, dialkyl tin organic acid salts, titanate, polyethylene glycol, chloroplatinic acid, zinc oxide, magnesium oxide, calcium oxide, barium oxide, aluminum oxide, calcium hydroxide, tin oxide, iron oxide, calcium hydroxide, calcium carbonate, magnesium carbonate, fatty acid sodium, calcium octylate, potassium isooctylate, potassium butoxide, cesium octylate, potassium isostearate, polyethylene glycol, polypropylene glycol, hexanediol, cyclohexanediol, dodecanediol, hexamethylene diamine, dodecane diamine, polyethylene glycol containing diamino at terminals, polypropylene glycol containing diamino at terminals, benzenedithiol, hexanedithiol, 1,10-decanedithiol, 1,12-dodecanedithiol, polyethylene glycol diacrylate, polyethylene glycol dimethacrylate, polypropylene glycol diacrylate, polypropylene glycol dimethacrylate, diallyl ether, triallyl isocyanurate, and triallyl cyanurate. The polymer having the three-dimensional net structure (e.g., heat-curable resin and crosslinked rubber) is obtainable in a manner that the crosslinking agents, the crosslinking acceralators, and/or the crosslinking assistants, each 0.1 to 20 parts by weight (preferably, 0.5 to 10 parts by weight), are added, for example, to the two-dimensional linear structural polymer (or low molecular monomer) of 100 parts by weight, and the resulting compound is subjected to a roll sheeting work, a calendar rolling work, a pressing work, an extruding work, or an injection molding work under conditions of a temperature of 20 to 350° C. for 0.1 second to 200 minutes. The polymer having the two-dimensional linear structure (e.g., thermoplastic resin and un-crosslinked rubber) is obtainable by a publicly known method. The photo-curing resin is obtainable by irradiating ultraviolet rays of a range between 200 and 400 nm to a composite constituting the photo-curing resin by using a UV device (e.g., high-pressure mercury UV lamps, low-pressure mercury UV lamps, fluorescence type UV lamps (short ARC xenon lamps and chemical lamps), and metal halide lamps) at a rate of 10 mJ/m²~20 kJ/m² in the air, in a nitrogen atmosphere, in an argon atmosphere, or under depressurization. The composite constituting the photo-curing resin contains, for example, the photopolymerization catalyst. An amount thereof is, for example, a range between 0.01 and 5 parts by weight per 100 parts by weight of the compound containing an epoxy group. In a case where a blending ratio of the photopolymerization catalyst is small, e.g., less than 0.01 parts by weight, the irradiation of light does not contribute to sufficient increase of the rate of the ring-opening reaction of the epoxy group. Blending ratio beyond 5 parts by weight does not contribute to improvement of the reaction. The vulcanized rubber is obtainable by leaving the composite containing a desired components such as a linear copolymer having a glass transition temperature equal to or less than −20° C., the crosslinking agent, and/or the crosslinking accelerator at a temperature of a range between 0 and 300° C. (preferably, a range between 60 and 180° C.) for 0.1 to 120 minutes (preferably, for 5 to 60 minutes). If the temperature is low, it takes too long for the reaction, resulting in inviting degradation of productivity. To the contrary, if the temperature is high, too much energy cost is required. Therefore, the treatment is to be performed under the above described conditions. A coating film is also exemplified as the high polymerized materials. However, the coating film is not solely used as the high polymerized material. Specifically, the coating film is used in the form of a composite material. Generally, the coating film is obtainable in a manner that the two-dimensional linear polymer (thermoplastic resin) is mixed with the crosslinking agent, the crosslinking accelerator, the crosslinking assistant, and a solvent and, subsequently, the resulting mixture is coated to be dried. The mixture is also polymerized, as required. The organic high polymerized material contains, as required, a filler and a functionality additive. The functionality additive is capable of exerting a desired function. The functionality additive can work as a reinforcer. Examples of the functionality additive include carbon black, calcium carbonate, talc, flat talc, mistron talc, clay, kaolin, flat kaolin, cellulose, celite, flat clay, kaolin, glass, barium titanate, strontium titanate, mica, and silica. Examples of the reinforcer include rayon, nylon, polyester, vinylon, steel, Kevlar, a carbon fiber, and a glass fiber. The reinforcer may be given in the form of fiber or fabric. Other examples of the reinforcer include powders of copper, nickel, silver, gold, tin, and carbon. Further, other examples of the reinforcer include the conductive materials. Still further, other examples of the reinforcer include heat transfer materials such as almina, silicon nitride, alumina nitride, silicon carbide, and diamond. An addition amount is decided according to an intended use thereof. Still further, stabilizers (e.g., antioxidants and ultraviolent ray inhibitors) are sometimes used as the reinforcer. The stabilizers contribute to enhancement of reliability of the high polymerized materials. Examples of the stabilizer include amine/ketone-based condensation products (e.g., poly(2,2,4-trimethyl-1,2-dihydroquinoline) and 6-ethoxy-1,2-dihydro-2,2,4-trimethylquinoline), secondary aromatic amine compounds (e.g., octyldiphenylamine, 4,4-bis(α,α-dimethylbenzyl)diphenylamine, N,N-diphenyl-p-phenylenediamine, N-phenyl-N'-isopropyl-p-phenylenediamine, N-phenyl-N'-isopropyl-1,3-dimethylbutyl-p-phenylenediamine), monophenol-based compound and bisphenol-based compound (e.g., styrenated phenol, 2,6-di-t-butyl-4-phenol, 2-t-butyl-6-(3-t-butyl-2-hydroxy-5-methylbenzyl)-4-methylphenylacrylate, 2,2-methylene bis(4-methyl-6-t-butylphenol), 4,4-thiobis(3-methyl-6-t-butylphenol), and 2,5-di-t-butylhydroquinone), 2-mercaptobenzimidazole, 2-Zn-mercaptobenzimidazole, nickel dimethyldithiocarbamate, 1,3-bis(dimethylaminopropyl)thiourea, dilauryl-3,3-thiodipropionate, tris(nonylated phenyl)phosphate, 2-(4-hydroxy-3,5-t-butyl)aniline-1,3,5-triazine-4,6-dithiol, 2-(4-phenylamino)aniline-1,3,5-triazine-4,6-dithiol, 2-(N-anilinophenyl)-N'-isopropylamino-1,3,5-triazine-4,6-dithiol, 4-di(N-anilinophenyl-N'-isopropylamino)-1,3,5-triazine-6-thiol, 2,4-di(N-anilinophenyl-N'-isopropylamino)-1,3,5-triazine-6-thiol, 1,3,5-triazine-2,4,6-trithiol, bis(2,4-dithiol-1,3,5-triazinyl-6-amino)benzene, and 2-triethoxysilylpropylamino-1,3,5-triazine-4,6-dithiol. Specifically, sulfur-based compound or phosphorus-based compound such as triazinethiol containing an antioxidant group is used as the stabilizer. An adding amount is decided according to an intended use thereof.

The composite material is a proper combination of the metal materials, the ceramic materials, and the high polymerized materials. For example, the composite material is formed such that a ceramic material is provided on a surface of a metal material. For example, the composite material is formed such that a high polymerized material is provided on a surface of a metal material. For example, the composite material is formed such that a metal material is provided on a surface of a ceramic material. For example, the composite material is formed such that a high polymerized material is provided on a surface of a ceramic material. In addition thereto, the composite material is formed with various combinations of materials. For example, the combination of the materials is configured by bonding of a material A and a material B. This, however, should not be construed in a limiting sense. In a case where the composite material is configured by bonding, each material is to be subjected to cleaning treatment in advance. Alternatively, each material is to be processed in advance by, for example, a silane coupling agent.

One substrate that was treated with the surface treatment agent is provided as an adhered, and the other substrate that was treated with the surface treatment agent (or that was not treated with the surface treatment agent) is provided as an adhesive. Bonding therebetween ensures obtainment of various types of composite products. Thus obtained material is immersed into (or sprayed with) electroless plating solution and, subsequently, subjected to electroplating. Accordingly, a plated product is obtained. It is also possible to form a circuit substrate in such a manner that a plated metalized product is coated with resist. Then, the resist is etched. Also, it is possible to form a hydrophobic (or hydrophilic) microchannel with ease in such a manner that a groove or a flow channel is formed on the surface of the substrate and, subsequently, the same materials are bonded together after the hydrophobic treatment (or after the hydrophilic treatment). If an additive property is imparted to the conductive composite body, the composite magnetic body, or the heat conductive composite, fluid bonding (treatment bonding or crosslink bonding) or non-fluid bonding (assembly bonding) of the metal materials, the ceramic materials, the high polymerized materials, or the composite high polymerized materials becomes possible. The present invention is effective in many industrial fields such as electronic equipment filed, a material field, an automobile field, a robot field, a building and a construction field, and an environment and energy field. Recently, multi-functionality, high performance, and downsizing are rapidly attained in digital equipment, portable/mobile equipment, high-frequency module equipment, and network devices. A SiP (System in Package) product which packages a plurality of chips such as a microcomputer, SoC, and memory in a single package, CoC products, and the like are expanding in market as a means for achieving this. Nowadays, a SiP technology for realizing higher performance and a higher functionality of equipment is demanded. To realize the high performance and the high functionality, improvement in bonding technology for bonding minute parts is essential. The present invention is also effective in such field.

Hereinafter, specific embodiments are exemplified to describe the present invention. However, the present invention should not be limited only to the following embodiments. Needless to say, the present invention may be modified to be carried out in various forms without departing from the technical concept of the present invention. Each of the embodiments and examples may be combined, as required, for carrying out the present invention.

EXAMPLE 1

6-(3-triethoxysilylpropyl)amino-1,3,5-triazine-2,4-dichloride (TEDC) and N,N'-bis(2-aminoethyl)-6-(3-triethoxysilylpropyl)amino-1,3,5-triazine-2,4-diamine (TEDDA) were synthesized according to the following Reaction Formula (1-1) and Reaction Formula (1-2)

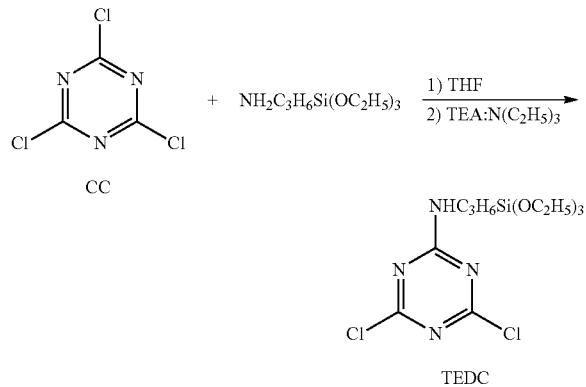

REACTION FORMULA 1-1

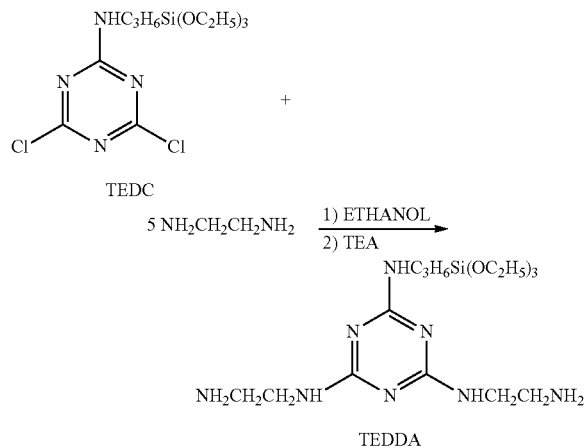

REACTION FORMULA 1-2

A stirring bar and cyanuric chloride (CC: 18.325 g; 99.37 mmol: produced by Kanto Chemical Industry Co., Ltd.) were placed in a three neck flask having a capacity of 500 mL. A thermometer and an addition funnel were attached thereto. An inside of the flask was placed in an argon atmosphere. Then, THF (200 mL) was added thereto. The flask was cooled down to a temperature of −20° C. Subsequently, 3-triethoxysilylpropylamine (28 mL; 120 mmol: produced by Chisso Corporation)/THF (20 mL: produced by Kanto Chemical Industry Co., Ltd.) solution was gradually dripped into the flask for 30 minutes. After the dripping thereof, triethylamine (17 mL; 122 mmol: produced by Wako Pure Chemical Industries, Ltd.)/THF (20 mL: produced by Kanto Chemical Industry Co., Ltd.) solution was gradually dripped thereinto for 30 minutes. After the dripping thereof, stirring was performed at a temperature of −20° C. for one hour. After the reaction thereof, triethylamine hydrochloride was filtered to be left as a byproduct. Then, condensation and vacuum drying were performed using a rotary evaporator. Accordingly, a crude product was obtained. The crude product was refined by a silica gel column chromatography (eluent: chloroform). Thus obtained purified product (6-(3-triethoxysilylpropyl)amino-1,3,5-triazine-2,4-dichloride (31.820 g; 84.96 mmol) was pale yellow oil. The NMR data and the like were shown below.

$^1$H NMR (400 MHz, CDCl$_3$) d 0.67 (t, J=8.0 Hz, 2H, CH$_2$CH$_2$Si), 1.24 (t, J=6.9 Hz, 9H, SiOCH$_2$CH$_3$), 1.73 (quint, J=8.0 Hz, 2H, CH$_2$CH$_2$CH$_2$), 3.49 (q, J=8.0 Hz, 2H, NHCH$_2$CH$_2$, 3.83 (q, J=6.9 Hz, 2H, SiOCH$_2$CH$_3$), 6.60 (brs, 1H, NH)

ELEMENT ANALYSIS: MEASUREMENT VALU (%); C: 38.81, N: 15.01, H: 6.02, CALCULATION VALUE (%, C$_{12}$N$_4$H$_{22}$O$_3$SiCl$_2$); C: 39.02, N: 15.17, H: 6.00.

Next, a stirring bar and ethylenediamine (11 mL; 165 mmol: produced by Tokyo Chemical Industry Co., Ltd.: refined by a molecular sieve) were placed in a three neck flask having a capacity of 300 mL. An inside of the flask was placed in an argon atmosphere. A mixed solution of 6-(3-triethoxysilylpropyl)amino-1,3,5-triazine-2,4-dichloride (7.821 g; 21.18 mmol) and THF (60 mL) was dripped thereinto. After the dripping thereof, the reaction solution thereof was gradually heated up to a temperature of 90° C. Then, the reaction was carried out for 17 hours, followed by cooling down to room temperature and suction filtration via celite. The filtrate was condensed by the rotary evaporator and depressurized to be dried. The condensed solution was subjected to refining by the silica gel column chromatography. Accordingly, N,N'-bis(2-aminoethyl)-6-(3-triethoxysilylpropyl)amino-1,3,5-triazine-2,4-diamine (TEDDA, 6.063 g; a yield of 69%) was obtained in the form of pale yellow oil. Thus obtained compound was identified by the element analysis, the NMR spectrum, and the MS measurement. An element analysis value N % was obtained by a Perkin Elmer Model 2400CHN analysis apparatus. The NMR spectrum measurement was performed by an AC400P made by Bruker Japan Co. Ltd. The MS was performed by a JMS-700 manufactured by JEOL LTD.

$^1$H NMR (400 MHz, DMSO-d$_6$) d 0.52 (br t, J=8.0 Hz, 2H, CH$_2$CH$_2$Si), 1.12 (t, J=7.0 Hz, 9H, SiOCH$_2$CH$_3$), 1.36 (br s, 4H, CH$_2$NH$_2$), 1.50 (br s, 2H, CH$_2$CH$_2$CH$_2$), 2.60 (br t, J=5.6 Hz, 4H, NCH$_2$CH$_2$N), 3.15 (br s, 6H, CH$_2$CH$_2$CH$_2$ and NCH$_2$CH$_2$N), 3.72 (q, J=7.0 Hz, 6H, SiOCH$_2$CH$_3$), 6.39 (br s, 3H, NHCH$_2$×3)

$^{13}$C NMR (101 MHz, DMSO-d$_6$) d 7.4, 18.2, 22.9, 41.6, 42.7, 43.6, 57.6, 165.6, 165.8

MS (70 eV) m/z 416 (M$^{+}$)

ELEMENT ANALYSIS: MEASUREMENT VALU (%) C: 46.06; N: 26.61, H: 8.48, CALCULATION VALUE(%, $C_{16}N_8H_{38}O_3Si$): C: 46.13, N: 26.90, H: 8.71.

EXAMPLE 2

The reaction was observed according to the following reaction formula.

REACTION FORMULA 2

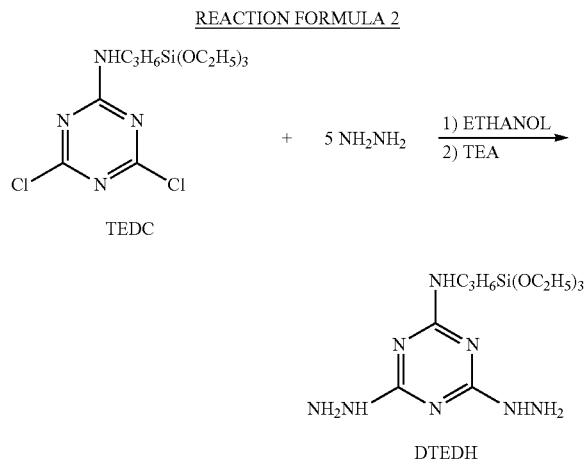

TEDC

DTEDH

A stirring bar and hydrazine-monohydrate (4.0 mL; 82 mmol: produced by Tokyo Chemical Industry Co., Ltd.) were placed in a three neck flask having a capacity of 200 mL. An inside of the flask was placed in an argon atmosphere. The flask was cooled down to a temperature of 0° C. Under this state, a mixed solution of 6-(3-triethoxysilylpropyl)amino-1,3,5-triazine-2,4-dichloride (3.734 g; 10.11 mmol) and ethanol (50 mL) was dripped into the flask. After dripping thereof, the reaction solution was gradually heated up to a temperature of 50° C. Then, reaction was carried out at a temperature of 50° C. for two hours. A precipitated white solid resulting from the reaction was filtered with suction filtering. The white solid was refined by a column chromatography. This ensured obtainment of 6-(3-triethoxysilylpropyl)amino-2,4-dihydrazinyl-1,3,5-triazine (DTEDH: 3.403 g; 9.44 mmol; a yield of 93%) in the form of colorless powder. When this compound was exposed to air, the compound absorbed carbon dioxide in the air to be precipitated. A result of the NMR analysis revealed that the compound was a target compound. The NMR data and the like were shown below.

$^1$H NMR (400 MHz, DMSO-$d_6$) d 0.53 (br t, J=8.0 Hz, 2H, C$\underline{H_2}$CH$_2$Si), 1.12 (t, J=6.9 Hz, 9H, SiOCH$_2$C$\underline{H_3}$), 1.50 (quint., J=8.0 Hz, 2H, CH$_2$C$\underline{H_2}$CH$_2$), 3.18 (br s, 2H, NCH$_2$CH$_2$, 3.31 (br s, 4H, NHN$\underline{H_2}$), 3.72 (q, J=6.9 Hz, 6H, SiOC$\underline{H_2}$CH$_9$), 6.73 (br s, 1H, N$\underline{H}$CH$_2$CH$_2$), 7.58 (br s, 2H, N$\underline{H}$NH$_2$;

$^{13}$C NMR (101 MHz, DMSO-$d_6$) d 7.3, 18.2, 22.8, 42.6, 57.6, 165.3, 167.4.

ELEMENT ANALYSIS: MEASUREMENT VALU (%); C: 40.12, N: 30.81; H, 7.68, CALCULATION VALUE (%, $C_{12}N_8H_{28}O_3Si$); C, 39.98, N, 31.09, H, 7.83.

EXAMPLE 3

REACTION FORMULA 4

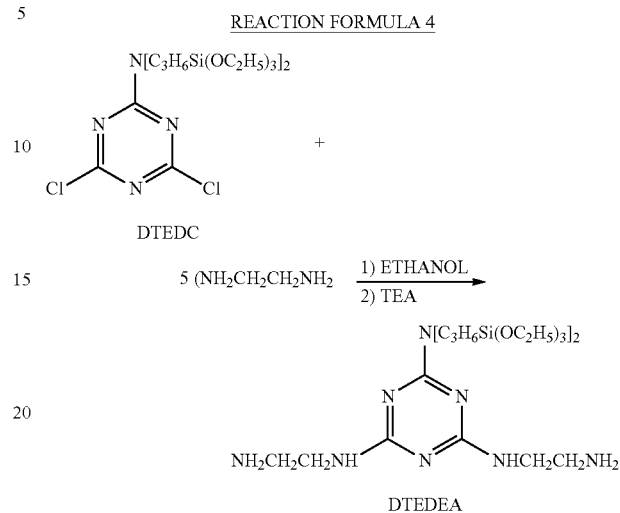

DTEDC

DTEDEA

DTEDC was synthesized from cyanuric chloride (CC) and di(N,N'-triethoxylylpropyl)amine. Then, the DTEDC was reacted with ethylenediamine in the presence of ethanol and triethylamine (TEA). The reaction solution was filtered. Subsequently, the solvent and the unreacted ethylenediamine were distilled under depressurization of a range between 1 and 10 mmHg. The resulting solution was dissolved in methanol solution to be bleached using activated carbon. The bleached solution was condensed and, subsequently, refined by the silica gel column chromatography. The condensation thereof ensured obtainment of light-yellow syrup. The light-yellow syrup was found to be 2-(N,N'-di-3-triethoxysilylpropyl)amino-4,6-di(2-aminoethyl) amino-1,3,5-triazine (DTEDEA) from the element analysis data, the NMR spectrum, and the others.

EXAMPLE 4

REACTION FORMULA 5-1

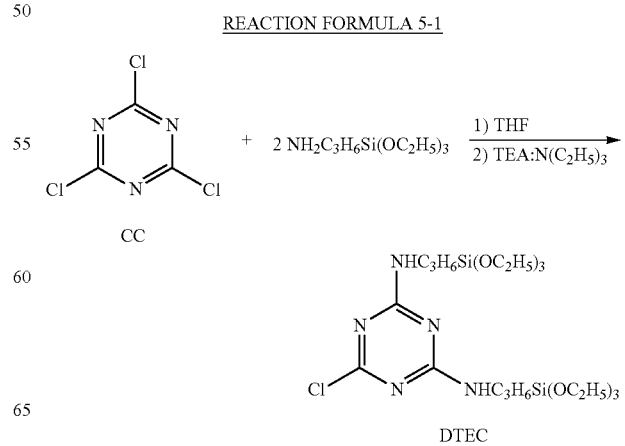

CC

DTEC

-continued

REACTION FORMULA 5-2

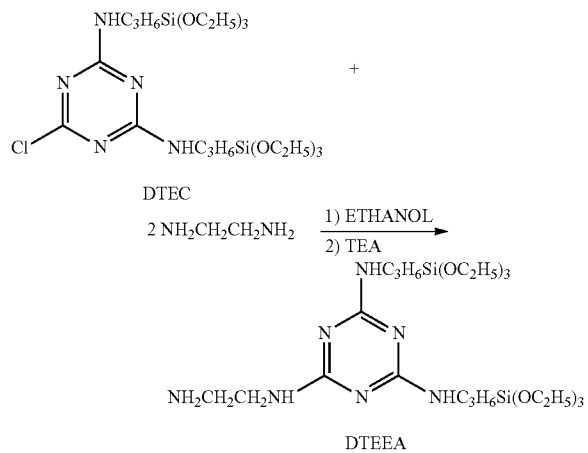

DTEC was synthesized from cyanuric chloride (CC) and di(triethoxysilylpropyl)amine. Then, reaction was carried out between the DTEC and ethylenediamine in the presence of ethanol and triethylamine (TEA). The reaction solution was filtered. The solvent and the unreacted ethylenediamine were distilled under depressurization by 10 mmHg. This was dissolved in methanol solution to be bleached using activated carbon. The bleached solution was condensed to be refined by the silica gel column chromatography. Condensation thereof ensured obtainment of light-yellow syrup. The light-yellow syrup was found to be 2-(2-aminoethyl)amino-4,6-di(3-triethoxysilylpropyl)amino-1,3,5-triazine (DTEEA) from the element analysis data, the NMR spectrum, and the others.

EXAMPLE 5

A case where the surface treatment using the compound (TEDDA) of the example 1 was performed will be described below.

A substrate of a size of 10 mm×20 mm×0.1 mm was prepared. The substrate is any one of a Ti plate, a Mo plate, a Ni plate, a Cu plate, an Al plate, an Ag plate, a Pt plate, a Sn plate, a SUS316 plate, and a brass plate. In other words, prepared were 10 different kinds of substrates. Each of the substrates was subjected to degreasing by ultrasonic wave in ethanol at a temperature of 40° C. for 15 minutes. Thereafter, the substrate was rinsed by ethanol in order to clean up the surface thereof. After the cleaning, the substrate was dried in a vacuum desiccator.

The post-treatment substrate was immersed in solution containing TEDDA (0.1 wt %). After a lapse of 10 minutes, the substrate was taken out. Subsequently, the substrate was further adequately rinsed by distilled water. Then, the substrate was left in the desiccator at a temperature of 20° C. under vacuum (equal to or less than 0.1 Hg) for 24 hours.

After the above described treatment, the post-TEDDA-treatment substrate was subjected to the XPS analysis. An X-ray photoelectron spectrometer (manufactured by ULVAC-PHI, INCORPORATED: PHI-Quntera SXM Scanning X-ray Microprobe, an irradiation angle of 45°) was used for the XPS analysis.

Instead of the TEDDA, aminopropyl triethoxysilane (APS: AIS0610.0 produced by AZmax Co.) was employed to provide the same treatment to the substrate as a comparison example.

A result of the XPS analysis is shown in the following Table-1.

TABLE 1

CONCENTRATION OF ELEMENT ON SURFACE OF METAL MATERIAL IMMERSED IN TEDDA SOLUTION OF 0.1%

|  | METAL | (at. %) | N (at. %) | O (at. %) | Si (at. %) |
|---|---|---|---|---|---|
| EXAMPLE 5 |  |  |  |  |  |
| EXAMPLE 5a | Ti | 4.1 | 20.4 | 18.7 | 3.0 |
| EXAMPLE 5b | Mo | 6.4 | 35.5 | 22.0 | 6.4 |
| EXAMPLE 5c | Ni | 1.4 | 24.1 | 14.3 | 3.4 |
| EXAMPLE 5d | Cu | 1.6 | 21.7 | 16.1 | 3.8 |
| EXAMPLE 5e | Al | 11.9 | 18.1 | 21.4 | 3.2 |
| EXAMPLE 5f | Ag | 15.2 | 16.6 | 12.8 | 1.8 |
| EXAMPLE 5g | Pt | 11.1 | 20.6 | 12.0 | 3.5 |
| EXAMPLE 5h | Sn | 3.1 | 24.8 | 15.4 | 2.7 |
| EXAMPLE 5i | SUS316 | 0.8/1.4 | 20.3 | 19.9 | 3.6 |
| EXAMPLE 5j | Cu/Zn | 0.4/0 | 28.4 | 11.2 | 4.4 |
| COMPARISON EXAMPLE 5 |  |  |  |  |  |
| COMPARISON EXAMPLE 5a | Ti | 14.2 | 0 | 42.2 | 0 |
| COMPARISON EXAMPLE 5b | Mo | 20.4 | 0 | 38.9 | 0 |
| COMPARISON EXAMPLE 5c | Ni | 13.1 | 0 | 29.4 | 0 |
| COMPARISON EXAMPLE 5d | Cu | 6.3 | 0.1 | 27.2 | 0 |
| COMPARISON EXAMPLE 5e | Al | 24.4 | 0 | 44.6 | 0 |
| COMPARISON EXAMPLE 5f | Ag | 39.3 | 0 | 13.5 | 0 |
| COMPARISON EXAMPLE 5g | Pt | 37.4 | 0.4 | 14.3 | 0 |
| COMPARISON EXAMPLE 5h | Sn | 30.6 | 0.2 | 39.3 | 0 |
| COMPARISON EXAMPLE 5i | SUS316 | 2.9/9.2 | 0 | 44.7 | 0 |
| COMPARISON EXAMPLE 5j | Cu/Zn | 6.6/1.5 | 0.2 | 31.5 | 0.2 |

Table-1 shows the following facts. In the post-TEDDA-treatment substrate, concentration of metal and concentration of oxygen of the surface of the substrate decrease as well as concentration of nitrogen and concentration of silicon remarkably increase, as a whole, in comparison with the post-APS-treatment substrate. This shows that the TEDDA is tightly absorbed (bonded) to the surface of the substrate, whereas the APS is hardly absorbed (bonded) to the surface of the substrate. In this analysis, the irradiation angle of X rays is 45°, and thus elements existing up to a depth of about 7 nm from the uppermost surface are measured. A sufficient amount of metal atoms are observed in the analysis of the surface of the post-TEDDA-treatment substrate, which shows that a thickness of a TEDDA film is equal to or less than 7 nm. Since the XPS analysis is performed under the condition of $10^{-6}$ Pa or less, it is understood that the TEDDA is absorbed (bonded) to the substrate with a bonding force (a bonding force corresponding to the bonding force of the chemical bonding) higher than a normal intermolecular force.

EXAMPLE 6

A case where the surface treatment using the compound (TEDDA) of the Example 1 was performed will be described below.

A substrate of a size of 10 mm×10 mm×0.1 mm was prepared. The substrate is any one of an almina plate, a silicon carbide plate, an aluminum nitride plate, a zinc oxide plate, a carbon plate, a glass plate, a zirconia plate, a porcelain plate, a cement plate, and a plaster plate. In other words, prepared were 10 different kinds of substrates. Then, treatment identical to the treatment of the Example 5 was performed.

Instead of the TEDDA, aminopropyl triethoxy silane (APS) was employed to provide the similar treatment to the substrate as a comparison example.

A result of the XPS analysis is shown in the following Table-2.

TABLE 2

CONCENTRATION OF ELEMENT ON SURFACE OF CERAMIC MATERIAL IMMERSED IN TEDDA SOLUTION OF 0.1%

| | CERAMICS | | (at. %) | N (at. %) | O (at. %) | Si (at. %) |
|---|---|---|---|---|---|---|
| EXAMPLE 6 | POST-TEDDA-TREATMENT CERAMICS | | | | | |
| EXAMPLE 6a | $Al_2O_3$ | Al | 4.1 | 17.1 | 22.4 | 3.2 |
| EXAMPLE 6b | SiC | C | 29.7 | 25.3 | 12.3 | 33.7 |
| EXAMPLE 6c | AlN | Al | 22.8 | 44.6 | 13.3 | 3.4 |
| EXAMPLE 6d | ZnO | Zn | 15.6 | 22.3 | 32.2 | 3.7 |
| EXAMPLE 6e | C | C | 49.1 | 24.8 | 21.3 | 4.8 |
| EXAMPLE 6f | $SiO_2$ | Si | 22.2 | 18.6 | 38.4 | — |
| EXAMPLE 6g | $ZrO_2$ | Zr | 11.1 | 20.6 | 12.0 | 3.5 |
| EXAMPLE 6h | PORCELAIN | Mg | 8.2 | 20.4 | 25.3 | 17.6 |
| EXAMPLE 6i | CEMENT | Ca | 17.3 | 16.3 | 35.3 | 4.2 |
| EXAMPLE 6j | PLASTER | Ca | 7.1 | 28.4 | 41.2 | 3.4 |
| COMPARISON EXAMPLE 6 | POST-APS-TREATMENT CERAMICS | | | | | |
| COMPARISON EXAMPLE 6a | $Al_2O_3$ | Al | 29.5 | 0 | 56.3 | 0 |
| COMPARISON EXAMPLE 6b | SiC | C | 54.7 | 0 | 0 | 45.3 |
| COMPARISON EXAMPLE 6c | AlN | Al | 43.8 | 42.6 | 0 | 0 |
| COMPARISON EXAMPLE 6d | ZnO | Zn | 38.2 | 0 | 42.3 | 0 |
| COMPARISON EXAMPLE 6e | C | C | 96.2 | 0 | 6.6 | 0 |
| COMPARISON EXAMPLE 6f | $SiO_2$ | Si | 29.6 | 0 | 53.8 | 0 |
| COMPARISON EXAMPLE 6g | $ZrO_2$ | Zr | 30.1 | 0 | 54.3 | 0 |
| COMPARISON EXAMPLE 6h | PORCELAIN | Mg | 21.3 | 0.2 | 32.3 | 20.3 |
| COMPARISON EXAMPLE 6i | CEMENT | Ca | 28.2 | 0 | 41.1 | 6.2 |
| COMPARISON EXAMPLE 6j | PLASTER | Ca | 14.3 | 0.2 | 60.2 | 0.2 |

Table-2 shows the following facts. In the post-TEDDA-treatment substrate, concentration of metal and concentration of oxygen of the surface decrease as well as concentration of nitrogen and concentration of silicon remarkably increase, as a whole, in comparison with the post-APS-treatment substrate (comparison example). Since the AlN plate is constituted of Al, and N and the SiC plate is constituted of Si and C, the above described trend is not remarkable. However, similar trend is seen. This shows that TEDDA is tightly absorbed (bonded) to the surface of the ceramic material. In this analysis, the irradiation angle of X rays is 45°, and, therefore, elements existing up to a depth of about 7 nm from the uppermost surface are measured. A sufficient amount of metal atoms is observed in the analysis of the surface of the post-TEDDA-treatment substrate, which shows that a thickness of the TEDDA film is equal to or less than 7 nm. Since the XPS analysis is performed under the condition of $10^{-6}$ Pa or less, it is understood that the TEDDA is absorbed (bonded) to the substrate with a bonding force (a bonding force corresponding to the bonding force of the chemical bonding) higher than a normal intermolecular force.

EXAMPLE 7

A case where the surface treatment using the compound (TEDDA) of the Example 1 was performed will be described below.

A substrate of a size of 10 mm×20 mm×0.2 mm was prepared. The substrate is any one of a polyethylene plate (PE: LD-PE: 07-127-01: produced by Hagitec Inc.), a polypropylene plate (PP: produced by KOKUGO CO., Ltd.: 07-175-04), a tetrafluoro ethylene plate (PTFE: NO. 903UL: produced by NITTO DENKO CORPORATION), a polyoxymethylene plate (POM: DURACON M25-44: produced by Polyplastics Co., Ltd.), a nylon plate (PA6: P07-142-04, produced by KOKUGO CO., Ltd.), a polyethylene-2,6-naphthalate plate (PEN: produced by Teijin DuPont Films Japan Limited: Teonex(R)), a polyethylene terephthalate plate (PET: produced by TORAYCON/TORAY INDUSTRIES INC.), a polyether ether ketone plate (PEEK: PEEK450G: produced by Yasojima Proceed Co., Ltd.), a polyphenylene sulphide plate (PPS: C-130SG: produced by Idemitsu Kosan Co., Ltd.), a polycarbonate plate (PC: 07-145-04: produced by KOKUGO CO., Ltd.), a polyimide plate (PI: Kapton, produced by DU PONT-TORAY CO., LTD.), and a urethane plate (UR: 07-007-01: produced by KOKUGO CO., Ltd.). Then, treatment identical to the treatment of the Example 5 was performed.

Instead of the TEDDA, aminoethyl aminopropyl triethoxy silane (AEPS, SIT8398.0 produced by AZmax Co.) was employed as a comparison example to provide the same treatment to the substrate.

A result of the XPS analysis is shown in the following Table-3.

TABLE 3

CONCENTRATION OF ELEMENT ON SURFACE OF POLYMER MATERIAL IMMERSED IN TEDDA SOLUTION OF 0.1%

| | POLYMER MATERIAL | | (at. %) | N (at. %) | O (at. %) | Si (at. %) |
|---|---|---|---|---|---|---|
| EXAMPLE 7 | POST-TEDDA-TREATMENT POLYMER MATERIAL | | | | | |
| EXAMPLE 7a | PE | C1s | 63.4 | 23.0 | 9.7 | 3.9 |
| EXAMPLE 7b | PP | C1s | 85.6 | 6.5 | 6.7 | 1.6 |
| EXAMPLE 7c | PTFE | C1s | 35.4 | 1.2 | 0.6 | 0.2 |
| EXAMPLE 7d | POM | C1s | 54.6 | 20.3 | 22.9 | 2.7 |
| EXAMPLE 7e | PA6 | C1s | 53.8 | 28.0 | 13.4 | 4.8 |
| EXAMPLE 7f | PEN | C1s | 57.5 | 25.5 | 38.4 | 4.3 |
| EXAMPLE 7g | PET | C1s | 64.2 | 11.2 | 19.0 | 5.5 |
| EXAMPLE 7h | PEEK | C1s | 71.6 | 13.7 | 11.7 | 2.5 |
| EXAMPLE 7i | PPS | C1s | 67.7 | 15.8 | 12.5 | 2.9 |
| EXAMPLE 7j | PC | C1s | 54.9 | 28.5 | 12.2 | 4.4 |
| EXAMPLE 7k | PI | C1S | 61.9 | 19.3 | 16.7 | 2.1 |
| EXAMPLE 7l | U | C1S | 57.2 | 26.4 | 12.2 | 4.2 |
| COMPARISON EXAMPLE 7 | POST-APS-TREATMENT POLYMER MATERIAL | | | | | |
| COMPARISON EXAMPLE 7a | PE | C1s | 99.7 | 0 | 0.1 | 0 |
| COMPARISON EXAMPLE 7b | PP | C1s | 99.8 | 0 | 0.2 | 0 |
| COMPARISON EXAMPLE 7c | PTFE | C1s | 33.3 | 0 | 0 | 0 |

TABLE 3-continued

CONCENTRATION OF ELEMENT ON SURFACE OF
POLYMER MATERIAL IMMERSED IN TEDDA SOLUTION OF 0.1%

| | POLYMER MATERIAL | | N (at. %) | O (at. %) | Si (at. %) |
|---|---|---|---|---|---|
| COMPARISON EXAMPLE 7d | POM | C1s | 52.8 | 0 | 47.6 | 0 |
| COMPARISON EXAMPLE 7e | PA6 | C1s | 75.0 | 11.2 | 13.8 | 0 |
| COMPARISON EXAMPLE 7f | PEN | C1s | 77.8 | 0 | 22.2 | 0 |
| COMPARISON EXAMPLE 7g | PET | C1s | 72.0 | 0 | 28.0 | 1.2 |
| COMPARISON EXAMPLE 7h | PEEK | C1s | 86.4 | 0 | 13.6 | 0 |
| COMPARISON EXAMPLE 7i | PPS | C1s | 85.7 | 0 | 0 | 0 |
| COMPARISON EXAMPLE 7j | PC | C1s | 84.2 | 0 | 15.8 | 0 |
| COMPARISON EXAMPLE 7k | PI | C1S | 70.6 | 6.8 | 22.3 | 0.3 |
| COMPARISON EXAMPLE 7l | U | C1S | 69.8 | 3.4 | 23.4 | 3.3 |

Table-3 shows the following facts. In the post-TEDDA treatment substrate, concentration of carbon and concentration of oxygen of the surface decrease as well as concentration of nitrogen and concentration of silicon remarkably increase in comparison with the post-AEPS treatment substrate (comparison example). The concentration of nitrogen remarkably increases by the TEDDA treatment in every case except for a case of AP6 containing nitrogen. Since resin containing silicon is not used, in the present invention, silicon is contained in all the cases. The PTFE has only a little bonding amount but apparently has a considerably strong adhesive force. This shows that the TEDDA is tightly absorbed to the surface of the resin material. In this analysis, the irradiation angle of X rays of 45° enables measurement of elements existing up to a depth of about 7 nm from the uppermost surface. This reveals that a thickness of a film of the TEDDA is equal to or less than 7 nm. Since the XPS analysis is performed under the condition of $10^{-6}$ Pa or less, it is understood that the TEDDA is absorbed (bonded) to the substrate with a bonding force (a bonding force corresponding to the bonding force of the chemical bonding) higher than a normal intermolecular force.

EXAMPLE 8

A case where the surface treatment using the compound (TEDDA) of the Example 1 was performed will be described below.

Ethylene propylene diene rubber (EPDM, JSR-EP), a silicone rubber plate (Q: SH-851U: produced by Dow Corning Toray Co., Ltd.), styrene butadiene rubber (SBR: Nipol 1500: produced by Zeon Corporation), nitrile-butadiene rubber (NBR: DN300: produced by Zeon Corporation), and fluororubber (FKM: G-901: produced by DAIKIN INDUSTRIES, Ltd.) were prepared. The above mentioned materials were mixed with FEF black (produced by Tokyo Zairyo Co., Ltd.), DCP, and ZnO to be kneaded by a two-roll machine. As a result, un-crosslinked rubber sheets each having a thickness of 2 mm were obtained. These un-crosslinked rubber sheets were stacked to be placed in a die and pressurized by a vacuum heating apparatus (produced by Mikado Technos Co., Ltd.: Vacuum Boy VM01-1010VM) under pressure of 2 MPa at a temperature of 160° C. for 30 minutes. Accordingly, crosslinking was performed. As a result thereof, rubber substrates made of each material were obtained. Then, treatment identical to the treatment of the Example 5 was performed.

Instead of the TEDDA, aminoethyl aminopropyl triethoxysilane (AEPS, SIT8398.0 produced by AZmax Co.) was employed as a comparison example to provide the same treatment to the substrate.

A result of the XPS analysis is shown in the following Table-4.

TABLE 4

CONCENTRATION OF ELEMENT ON SURFACE OF CROSSLINKED
RUBBER MATERIAL IMMERSED IN TEDDA SOLUTION OF 0.1%

| | CROSSLINKED RUBBER MATERIAL | N (at. %) | O (at. %) | Si (at. %) |
|---|---|---|---|---|
| EXAMPLE 8 | POST-TEDDA-TREATMENT CROSSLINKED RUBBER MATERIAL | | | |
| EXAMPLE 8a | EPDM | 17.1 | 22.4 | 3.2 |
| EXAMPLE 8b | Q | 6.4 | 18.5 | 12.4 |
| EXAMPLE 8c | SBR | 44.6 | 13.3 | 3.4 |
| EXAMPLE 8d | NBR | 22.3 | 32.2 | 3.7 |
| EXAMPLE 8e | FKM | 24.8 | 21.3 | 4.8 |
| COMPARISON EXAMPLE 8 | POST-APS-TREATMENT CROSSLINKED RUBBER MATERIAL | | | |
| COMPARISON EXAMPLE 8a | EPDM | 0.3 | 8.8 | 0.7 |
| COMPARISON EXAMPLE 8b | Q | 0 | 26 | 24.1 |
| COMPARISON EXAMPLE 8c | SBR | 0.2 | 1.2 | 0.4 |
| COMPARISON EXAMPLE 8d | NBR | 6.8 | 2.3 | 0 |
| COMPARISON EXAMPLE 8e | FKM | 0 | 0.9 | 0 |

Table-4 shows the following facts. In the crosslinked rubber materials, Q (crosslinking silicone rubber) contains silicon, and NBR contains nitrogen, respectively, as a component of the material. However, other rubbers do not contain silicon or nitrogen. Therefore, in the analysis of surfaces of the post-TEDDA-treatment substrate and the untreated substrate, it is understood that presence and increase of N and Si reveals presence of the TEDDA on the surface by reaction with (or tight absorption to) the crosslinked rubber. It is a surprise that the TEDDA is bonded (absorbed) to rubbers having surfaces of which molecular chains are perturbated.

EXAMPLE 9

A case where the surface treatment using the compound (TEDDA) of the Example 1 was performed will be described below.

The substrate is made of a composite material. In other words, fillers listed in Table-5 were blended with high polymerized materials such as Q, PE, SBR, PA6, and PPS. The blend of fillers with respect to Q and SBR was performed by a two-roll machine, and the blend of fillers with respect to PE and PA6 was performed by a kneader, respectively. Further, press molding was performed using a die at a temperature of a range between 120° C. and 180° C. for five minutes. As a result, a substrate of a size of 10 mm×20 mm×0.1 mm was obtained. Then, treatment identical to the treatment of the Example 5 was performed.

Instead of the TEDDA, aminoethyl aminopropyl triethoxysilane (AEPS, SIT 8398.0 produced by AZmax Co.) was employed as a comparison example to provide the same treatment to the substrate.

A result of the XPS analysis is shown in the following Table-5.

TABLE 5

CONCENTRATION OF ELEMENT ON SURFACE OF COMPOSITE MATERIAL IMMERSED IN TEDDA SOLUTION OF 0.1%

| | POLYMER MATERIAL | FILLER | N (at. %) | O (at. %) | Si (at. %) |
|---|---|---|---|---|---|
| EXAMPLE 9 | | POST-TEDDA-TREATMENT COMPOSITE MATERIAL | | | |
| EXAMPLE 9a | Q | $Al_2O_3$: 1000 phr | 8.6 | 38.4 | 3.6 |
| EXAMPLE 9b | PE | MICA: 200 phr | 20.6 | 12.0 | 3.5 |
| EXAMPLE 9c | SBR | MICA: 100 phr | 20.4 | 25.3 | 17.6 |
| EXAMPLE 9d | PA6 | CLAY: 100 phr | 16.3 | 35.3 | 4.2 |
| EXAMPLE 9e | PPS | $SiO_2$: 40 phr | 14.4 | 41.2 | 12.6 |
| COMPARISON EXAMPLE 9 | | POST-APS-TREATMENT COMPOSITE MATERIAL | | | |
| COMPARISON EXAMPLE 9a | Q | SAME EXAMPLE | 0 | 53.8 | 2.3 |
| COMPARISON EXAMPLE 9b | PE | SAME EXAMPLE | 0 | 54.3 | 0 |
| COMPARISON EXAMPLE 9c | SBR | SAME EXAMPLE | 0.2 | 32.3 | 20.3 |
| COMPARISON EXAMPLE 9d | PA6 | SAME EXAMPLE | 0 | 41.1 | 6.2 |
| COMPARISON EXAMPLE 9e | PPS | SAME EXAMPLE | 0.2 | 24.2 | 13.8 |

Table-5 shows the following facts. In the composite material, Q (crosslinked silicone rubber) contains Si as a constituting component, and NBR contains N as a constituting component, respectively. However, the others do not contain Si or N. Therefore, in the analysis of surfaces of the post-TEDDA-treatment composite material and the untreated composite material, presence and increase of N and Si reveal presence of the TEDDA on the surfaces of the composite materials by reaction (or tight absorption) therebetween.

EXAMPLE 10

The substrate of the Example 5d (post-TEDDA-treatment Cu plate), the substrate of the Example 5e (post-TEDDA-treatment Al plate), the substrate of the Example 5i (post-TEDDA-treatment SUS316 plate), the substrate of the Example 6f (post-TEDDA-treatment $SiO_2$ plate), the PI plate that was subjected to the treatment identical to that of the Example 7 (P1: kapton, produced by DU PONT-TORAY CO., LTD.), and the UR plate that was subjected to the treatment identical to that of the Example 7 (UR: 07-007-01: produced by KOKUGO CO., Ltd.) were prepared.

The Cu plate employed in the Example 5d, the PP plate employed in the Example 7b, and the Q plate employed in the Example 8b were prepared. No TEDDA treatment was provided thereto. The substrates were subjected to degreasing by ultrasonic wave (in ethanol at a temperature of 40° C. for 15 minutes). Then, the substrates were rinsed by ethanol. The substrates were further subjected to corona discharge treatment (using corona master produced by Shinko Electric & Measurement Co., Ltd., output voltage; 9 kV (surface voltage), oscillating frequency: 20 kHz, temperature: 20° C.).

The post-TEDDA-treatment substrate and the TEDDA-untreatment substrate were placed facing to each other having the TEDDA film therebetween. Then, the substrates were pressurized by 1 MPa at a temperature of 120° C. for 10 minutes.

A P1 plate (P1: kapton, produced by DU PONT-TORAY CO., LTD.) that was subjected to the same treatment of the Example 7 and a substrate of the Example 5i (post-TEDDA-treatment SUS316 plate) were prepared.

The post-TEDDA-treatment SUS316 plate (substrate of the Example 5i) was coated with acryl urethane-based coating (U: Urecco Coat, produced by FUKUGOSHIZAI CO., LTED.). Then, the plate was subjected to hardening treatment (50° C.; 24 hours). Subsequently, similar to the Example 5i, a surface of an acrylurethan-based coated film was subjected to surface treatment with TEDDA solution.

The post-TEDDA-treatment substrate was immersed (temperature: 25° C., time: 1 minute) in a catalyst treatment solution (NP-8 produced by C. Uyemura & Co., Ltd.; 150 mL/L HCl; 150 mL/L). Accordingly, the substrate comes to carry a Pd—Sn catalyst on its surface. The substrate carrying the Pd—Sn catalyst thereon was immersed (temperature: 33° C., time: 20 minutes) in an electroless copper plating bath (THRU-CUP PSY-1A; 100 ml/L, THRU-CUP PSY-1B; 55 ml/L manufactured by C. Uyemura & Co., Ltd., formalin solution of 18.5%; 20 mL/L). Thereafter, the substrate was subjected to electroplating. The electroplating bath employed in the electroplating was any one of a THRU-CUP ETN bath (CuSO4.5H2O; 80 g/L H2SO4; 200 g/L Cl—; 50 ppm), a THRU-CUP ETN-1A bath (1 ml/L), and a THRU-CUP ETN-1B bath (10 ml/L) manufactured by C. Uyemura & Co., Ltd. The electroplating was performed at an electrical current of 2.5 A/dm2 for 60 minutes at a temperature of 25° C. Thus obtained Cu plating film had a thickness of 30 μm.

Instead of the TEDDA, an AEPS (produced by AZmax Co.) was employed as a comparison example to provide the same treatment to the substrate.

The following measurement was performed for a sample obtained by the present example. A result thereof is shown in Table-6. A debonding test apparatus (autograph P-100 manufactured by Shimadzu Corporation) was employed for measuring bonding strength (adhesion strength). A peeling rate at the time of measurement was 5 mm/min.

TABLE 6

PEELING RATE AND COVERAGE OF COMPOSITE MATERIAL BY TEDDA SOLUTION OF 0.1%

| | | | ADHESIVE PROPERTY | |
|---|---|---|---|---|
| EXAMPLE | SUBSTRATE | ADHESIVE | ADHESIVE STRENGTH (kN/m) | COVERAGE (%) |
| EXAMPLE 10a(COMPARISON EXAMPLE 10a) | SUS316 | Q | 1.5(0) | 100(0) |

TABLE 6-continued

PEELING RATE AND COVERAGE OF COMPOSITE MATERIAL BY TEDDA SOLUTION OF 0.1%

| EXAMPLE | SUBSTRATE | ADHESIVE | ADHESIVE STRENGTH (kN/m) | COVERAGE (%) |
|---|---|---|---|---|
| EXAMPLE 10b(COMPARISON EXAMPLE 10b) | Al | Q | 1.6(0) | 100(0) |
| EXAMPLE 10c(COMPARISON EXAMPLE 10c) | Cu | PP | 2.5(0.1) | 100(0) |
| EXAMPLE 10d(COMPARISON EXAMPLE 10d) | SiO2 | Q | 1.5(0) | 100(0) |
| EXAMPLE 10e(COMPARISON EXAMPLE 10e) | PI | Cu(FOIL) | 2.3(0.2) | 100(0) |
| EXAMPLE 10f(COMPARISON EXAMPLE 10f) | UR | Q | 1.5(0) | 100(0) |
| EXAMPLE 10g(COMPARISON EXAMPLE 10g) | PI | Cu(PLATING) | 1.6(0.2) | 100(0) |
| EXAMPLE 10h(COMPARISON EXAMPLE 10h) | U | Cu(PLATING) | 1.0(0.1) | 100(0) |

The Table-6 reveals that each sample according to the present invention has a remarkably large bonding strength (adhesion strength).

EXAMPLE 11

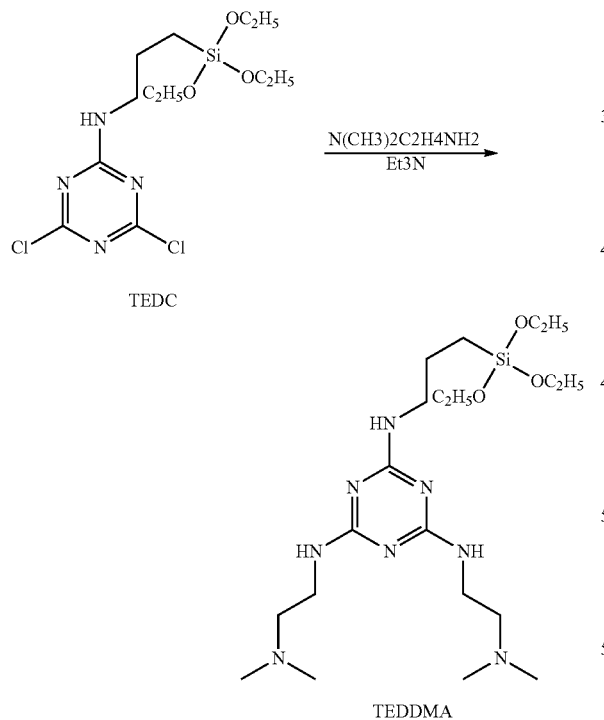

A stirring bar and N,N-dimethyl ethylenediamine (20.0 g; 0.230 mmol) were placed in a three neck flask having a capacity of 500 mL. An inside of the flask was placed in an argon atmosphere. A THF (200 mL) was added thereto. A mixture solution of 6-(3-triethoxysilylpropyl)amino-1,3,5-triazine-2,4-dichloride (8.3 g; 22.5 mmol) and the THF (100 mL) was dripped thereinto. After the dripping thereof, the reaction solution was gradually heated up to 90° C. Then, the reaction was carried out for eight hours, followed by cooling down to room temperature and suction filtration via celite. The filtrate was condensed by using the rotary evaporator and, subsequently, subjected to depressurized drying. This ensures obtainment of N,N'-bis(2-dimethylaminoethyl)-6-(3-triethoxysilylpropyl)amino-1,3,5-triazine-2,4-diamine (9.1 g; a yield of 86%) in the form of pale yellow oil. Thus obtained compound was identified by the element analysis, the NMR spectrum, and the MS measurement. The element analysis value N % was obtained by a Perkin Elmer Model 2400CHN analysis apparatus. The NMR spectrum measurement was performed by an AC400P manufactured by Bruker Japan Co. Ltd. The MS was performed by a JMS-700 manufactured by JEOL LTD.

$^1$H NMR (400 MHz, CDCl$_3$) d 0.65 (t, 2H, CH$_2$C$\underline{H}_2$Si), 1.22 (t, 9H, SiOCH$_2$C$\underline{H}_3$), 1.66 (quint, 2H, CH$_2$C$\underline{H}_2$CH$_2$), 2.29 (s, 12H, CH$_2$NC$\underline{H}_3$), 2.57 (t, 4H, NHCH$_2$C$\underline{H}_2$), 3.34-3.40 (m, 6H, NHC$\underline{H}_2$CH$_2$), 3.82 (q, 6H, SiOC$\underline{H}_2$CH$_3$).

$^{13}$C NMR (101 MHz, CDCl$_3$) d 7.7, 18.2, 23.1, 37.7, 37.9, 43.2, 45.1, 58.2, 165.5, 165.9.

MS (CI+) m/z 472 (M+1)

ELEMENT ANALYSIS: MEASUREMENT VALUE (%); C: 50.78, N: 23.61, H: 9.45 CALCULATION VALUE (%, C$_{20}$H$_{44}$N$_8$O$_3$SO; C: 50.82, N: 23.70, H: 9.38.

EXAMPLE 12

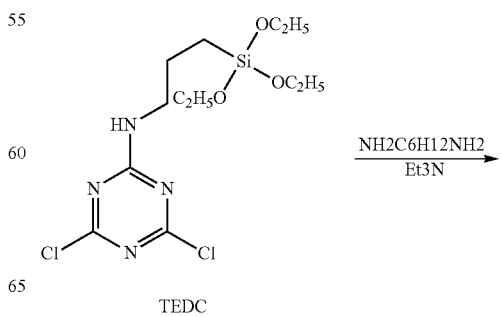

-continued

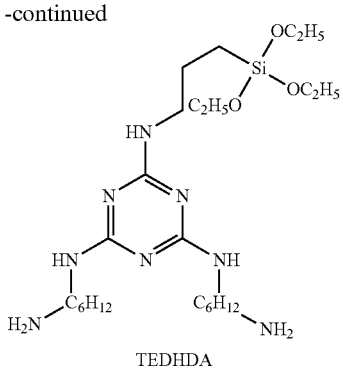

TEDHDA

A stirring bar and 1,6-hexanediamine (46.5 g; 0.40 mol) were placed in a three neck flask having a capacity of 300 mL. An inside of the flask was placed in an argon atmosphere. THF (80 g) was added thereto. A mixture of 6-(3-triethoxysilylpropyl)amino-1,3,5-triazine-2,4-dichloride (14.8 g; 0.04 mol) and THF (20 g) was dripped thereinto. After the dripping thereof, the reaction solution was gradually heated. Then, the reaction was carried out for five hours under reflex, followed by cooling down to room temperature and suction filtration via celite. The filtrate was condensed by the rotary evaporator and subjected to depressurized drying. As a result, N,N'-bis(2-aminohexyl)-6-(3-triethoxysilylpropyl)amino-1,3,5-triazine-2,4-diamine (TEDHDA, 19.9 g; a yield of 94%) was obtained in the form of pale yellow oil. The obtained compound was identified by the element analysis, the NMR spectrum, and the MS measurement. An element analysis value N % was obtained by the Perkin Elmer Model 2400CHN analysis apparatus. The NMR spectrum measurement was performed by the AC400P made by Bruker Japan Co. Ltd. The MS was performed by the JMS-700 manufactured by JEOL LTD.

$^1$H NMR (400 MHz, CDCl$_3$) d 0.66 (t, 2H, CH$_2$CH$_2$Si), 1.22 (t, 9H, SiOCH$_2$CH$_3$), 1.34-1.54 (m, 16H, CH$_2$—(CH$_2$)$_4$—CH$_2$), 1.66 (t, 2H, CH$_2$CH$_2$Si), 2.67 (t, 4H, CH$_2$CH$_2$NH$_2$), 3.32 (brs, 6H, NHCH$_2$CH$_2$), 3.81 (q, 6H, SiOCH$_2$CH$_3$).

$^{13}$C NMR (101 MHz, CDCl$_3$) d 7.7, 18.2, 23.1, 26.6, 29.8, 33.8, 40.5, 42.1, 43.2, 57.86, 58.2, 166.1.

MS (FAB+) m/z 529 (M$^+$+1)

ELEMENT ANALYSIS: MEASUREMENT VALUE (%); C: 54.62, N: 21.01, H: 10.01 CALCULATION VALUE (%, C$_{24}$H$_{52}$N$_8$O$_3$Si); C: 54.51, N: 21.19, H: 9.91.

EXAMPLE 13

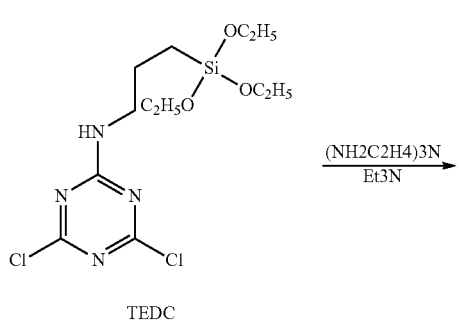

TEDC

-continued

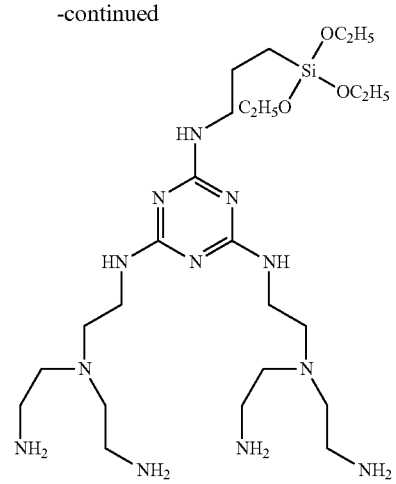

TEBTTA

A stirring bar and tris(2-aminoethyl)amine (29.3 g; 0.20 mmol) were placed in a three neck flask having a capacity of 300 mL. An inside of the flask was placed in an argon atmosphere. THF (40 g) was added thereto. A mixture of 6-(3-triethoxysilylpropyl)amino-1,3,5-triazine-2,4-dichloride (7.8 g; 0.02 mol) and THF (10 g) was dripped thereinto. After the dripping thereof, the reaction solution was gradually heated up to 90° C. Then, the reaction was carried out for eight hours, followed by cooling down to room temperature and suction filtration via celite. The filtrate was condensed by the rotary evaporator and, subsequently, subjected to depressurized drying. Accordingly, N,N'-bis{2-[bis-(2-aminoethyl)amino-]ethyl}-6-(3-triethoxysilylpropyl)amino-1,3,5-triazine-2,4-diamine (TEBTTA, 11.2 g; a yield of 95%) was obtained in the form of pale yellow oil. Thus obtained compound was identified by the element analysis, the NMR spectrum, and the MS measurement. An element analysis value N % was obtained by the Perkin Elmer Model 2400CHN analysis apparatus. The NMR spectrum measurement was performed by the AC400P manufactured by Bruker Japan Co. Ltd. The MS was performed by the JMS-700 manufactured by JEOL LTD.

$^1$H NMR (400 MHz, DMSO-d$_6$) d 0.53 (brs, 2H, CH$_2$CH$_2$Si), 1.06 (t, 8H, CH$_2$CH$_2$NH$_2$), 1.13 (t, 9H, SiOCH$_2$CH$_3$), 1.51 (brs, 2H, CH$_2$NCH$_2$CH$_2$NH$_2$), 2.36-2.54 (m, 20H, CH$_2$NCH$_2$CH$_2$NH$_2$), 3.23 (m, 6H, NHCH$_2$CH$_2$), 3.72 (q, 6H, SiOCH$_2$CH$_3$), 6.12-6.48 (m, 3H, NH)

$^{13}$C NMR (101 MHz, DMSO-d$_6$) d 7.8, 18.6, 23.3, 54.3, 56.4, 58.1, 58.4, 79.6, 166.1.

MS (FAB+)m/z 588 (M+1)

ELEMENT ANALYSIS: MEASUREMENT VALUE (%); C: 48.88, N: 28.55, H: 9.47 CALCULATION VALUE (%, C$_{24}$H$_{56}$N$_{12}$O$_3$Si; C: 48.95, N: 28.54, H: 9.59.

EXAMPLE 14

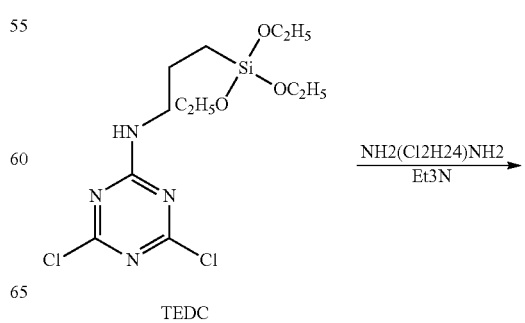

TEDC

-continued

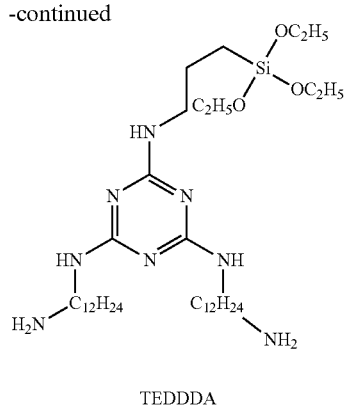

TEDDDA

A stirring bar and 1,12-dodecanediamine (40.1 g; 0.20 mol) were placed in a three neck flask having a capacity of 500 mL. An inside of the flask was placed in an argon atmosphere. THF (200 g) was added thereto. A mixture of 6-(3-triethoxysilylpropyl)amino-1,3,5-triazine-2,4-dichloride (7.8 g; 0.02 mol) and THF (10 g) was dripped thereinto. After the dripping thereof, the reaction solution was gradually heated. Then, the reaction was carried out for 10 hours under reflux, followed by cooling down to room temperature and suction filtration via celite. The filtrate was condensed by the rotary evaporator. Thereafter, the filtrate was subjected to depressurized drying. As a result, N,N'-bis(12-aminododecyl)-6-(3-triethoxysilylpropyl)amino-1,3,5-triazine-2,4-diamine (TEDDDA, 13.1 g; a yield of 94%) was obtained in the form of colorless oil. The obtained compound was identified by the element analysis, the NMR spectrum, and the MS measurement. An element analysis value N % was obtained by the Perkin Elmer Model 2400CHN analysis apparatus. The NMR spectrum measurement was performed by the AC400P manufactured by Bruker Japan Co. Ltd. The MS was performed by the JMS-700 manufactured by JEOL LTD.

$^1$H NMR (400 MHz, CDCl$_3$) d 0.65 (t, 2H, CH$_2$C$\underline{H}_2$Si), 1.20 (t, 9H, SiOCH$_2$C$\underline{H}_3$), 1.26-1.51 (m, 2H, CH$_2$C$\underline{H}_2$CH$_2$), 1.66 (brs, 2H, C$\underline{H}_2$CH$_2$Si), 2.67 (t, 4H, CH$_2$C$\underline{H}_2$NH$_2$), 3.31 (brs, 6H, NHC$\underline{H}_2$CH$_2$), 3.82 (q, 6H, SiOC$\underline{H}_2$CH$_3$).

$^{13}$C NMR (101 MHz, CDCl$_3$) d 7.6, 8.7, 18.2, 23.1 26.8, 29.5, 30.2, 33.7 40.5, 42.1, 43.16, 57.3 58.3 165.9

MS (FAB+) m/s 697 (M$^+$+1)

ELEMENT ANALYSIS: MEASUREMENT VALUE (%); C: 54.62, N: 21.01, H: 10.01 CALCULATION VALUE (%, C$_{24}$H$_{52}$N$_8$O$_3$Si); C: 54.51, N: 21.19, H: 9.91.

Meanwhile, other compounds listed in the above described [0022] are synthesized in the same manner.

EXAMPLE 15

The Cu plate employed in the Example 5d was prepared. The TEDDA (Example 1), the DTEDH (Example 2), the DTEDEA (Example 3), the DTEEA (Example 4), the TEDDMA (Example 11), the TEDHDA (Example 12), the TEBTTA (Example 13), and the TEDDDA (Example 14) were employed. The Cu plate was subjected to the surface treatment identical to that of the Example 5.

The PP plate employed in the Example 7b was prepared. The PP plate was not subjected to treatment using compound α. The substrate was subjected to the degreasing by ultrasonic wave (in ethanol at a temperature of 40° C. for 15 minutes). Subsequently, the substrate was rinsed by ethanol. Further, the substrate was subjected to corona discharge treatment (corona master manufactured by Shinko Electric & Measurement Co., Ltd., output voltage; 9 kV (surface voltage), oscillating frequency: 20 kHz, temperature: 20° C.).

A post-treatment Cu substrate made of each of the above described compounds and a untreated PP substrate were placed facing to each other having each compound film placed therebetween. Then, the substrate was pressurized at 1 MPa at a temperature of 120° C. for 10 minutes.

A P1 plate (P1: kapton, produced by DU PONT-TORAY CO., LTD.) was prepared. The TEDDA (Example 1), the TEDHDA (Example 12), the TEBTTA (Example 13), and the TEDDDA (Example 14) were employed to perform surface treatment identical to that of the Example 5.

The post-treatment substrate was immersed (temperature: 25° C., time: one minute) in a catalyst treatment solution (NP-8 produced by C. Uyemura & Co., Ltd.; 150 mL/L, HCl; 150 mL/L). Accordingly, the substrate comes to carry a Pd—Sn catalyst on its surface. The substrate carrying the Pd—Sn catalyst thereon was immersed (temperature: 33° C., time: 20 minutes) in an electroless copper plating bath (THRU-CUP PSY-1A; 100 ml/L, THRU-CUP PSY-1B; 55 ml/L each manufactured by C. Uyemura & Co., Ltd., formalin solution of 18.5%; 20 mL/L). Subsequently, the substrate was subjected to electroplating. The electroplating bath used in this electroplating was a THRU-CUP ETN bath (CuSO4.5H2O; 80 g/L, H2SO4; 200 g/L, Cl—; 50 ppm), a THRU-CUP ETN-1A bath (1 ml/L), or a THRU-CUP ETN-1B bath (10 ml/L) each manufactured by C. Uyemura & Co., Ltd. The electroplating was performed at an electrical current of 2.5 A/dm2 for 60 minutes at a temperature of 25° C. A thickness of thus obtained Cu plating film was 30 μm.

Samples obtained in the present example were subjected to the following measurement and results thereof are shown in Table-7. A debonding test apparatus (autograph P-100 manufactured by Shimadzu Corporation) was employed for measurement of bonding strength (adhesion strength). A peeling rate at the time of measurement was 5 mm/min.

TABLE 7

PEELING RATE AND COVERAGE OF COMPOSITE MATERIAL BY COMPOUND A SOLUTION OF 0.1%

| EXAMPLE 15 | COMPOUND α | SUBSTRATE | ADHESIVE | ADHESIVE STRENGTH (kN/m) | COVERAGE (%) |
|---|---|---|---|---|---|
| EXAMPLE 15a | DTEDH | Cu | PP | 1.6 | 80 |
| EXAMPLE 15b | DTEDEA | Cu | PP | 1.9 | 80 |
| EXAMPLE 15c | DTEEA | Cu | PP | 2.0 | 90 |
| EXAMPLE 15d | TEDDMA | Cu | PP | 1.9 | 90 |

TABLE 7-continued

PEELING RATE AND COVERAGE OF COMPOSITE
MATERIAL BY COMPOUND A SOLUTION OF 0.1%

| EXAMPLE 15 | COMPOUND α | SUBSTRATE | ADHESIVE | ADHESIVE PROPERTY | |
|---|---|---|---|---|---|
| | | | | ADHESIVE STRENGTH (kN/m) | COVERAGE (%) |
| EXAMPLE 15e | TEDHDA | Cu | PP | 2.2 | 100 |
| EXAMPLE 15f | | PI | Cu(PLATING) | 0.6 | 100 |
| EXAMPLE 15g | TEBTTA | Cu | PP | 2.6 | 100 |
| EXAMPLE 15h | | PI | Cu(PLATING) | 0.7 | 100 |
| EXAMPLE 15i | TEDDDA | Cu | PP | 2.5 | 100 |
| EXAMPLE 15j | | PI | Cu(PLATING) | 1.2 | 100 |
| EXAMPLE 15k | TEDDA | Cu | PP | 2.5 | 100 |
| EXAMPLE 15l | | PI | Cu(PLATING) | 1.6 | 100 |

Table-7 shows that each sample according to the present invention has remarkably large bonding strength (adhesion strength).

The measurement was performed in a manner identical to that of the Example 1 except that the ethylenediamine (11 mL) was changed to ethylenediamine (7 mL). As a result, a mixture of monomer of TEDDA and dimer of TEDDA (see, the General Formula shown above) was obtained. In other words, a mixture of monomer and dimer (a rate of mixture varied according to an amount of ethylenediamine) was obtained. It was not easy to isolate the dimer from the mixture. Surface treatment was performed by the mixture in a manner identical to that of the Example 5. A result of the surface treatment was close to the result of the surface treatment of the Example 5.

The surface treatment agent of the present invention is applicable to many kinds of substrates. That is, the surface treatment agent of the present invention has diversity.

The compound α coated on the surface of the substrate is rich in reactivity. It is possible to use the compound α in many fields with the use of the reactivity. For example, it is easy to provide a compound X capable of reacting with (absorbing to) the compound α on the substrate.

It is appreciated that the present invention is applicable to various fields (e.g., ornaments, electrical circuit substrates, and other composite products).

The invention claimed is:

1. A surface treatment method, comprising:
applying a compound α to a substrate;
wherein the compound α is at least one of Formula [IV] and Formula [V]:

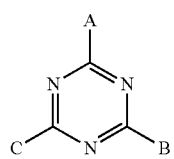

Formula [IV]

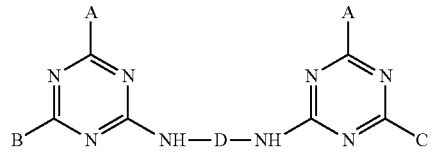

Formula [V]

wherein
A is $-N(R^a)R^b-Si(R^c)_n(OR^d)_{3-n}$, or $-N\{R^b-Si(R^c)_n(OR^d)_{3-n}\}_2$
B is $-NHNH_2$, $-N(R^e)R^f(NH_2)_m$, or $-N\{R^f(NH_4)_m\}_2$
C is A, B, or $-N(R^g)R^h$
D is $R^i$
wherein each of $R^a$, $R^e$ and $R^g$ is independently H or a hydrocarbon group consisting of H and C atoms,
$R^b$, $R^c$, $R^d$, $R^f$, $R^h$, and $R^i$ are hydrocarbon groups consisting of H and C atoms,
n is 0, 1, or 2, and
m is 1 or 2.

2. The surface treatment method according to claim 1, wherein applying the compound α comprises coating a solution comprising the compound α onto the substrate.

3. The surface treatment method according to claim 1, wherein applying the compound α comprises evaporation of the compound α.

4. The surface treatment method according to claim 1, further comprising before application of the compound α, subjecting the substrate to at least one treatment selected from the group consisting of a cleaning treatment, a corona discharge treatment, a plasma discharge treatment, an ultraviolet ray irradiation, an acid treatment, an alkaline treatment, a steam treatment, and a chemical conversion coating.

5. The surface treatment method according to claim 1, further comprising after application of the compound α, subjecting the substrate to a heating treatment.

6. The surface treatment method according to claim 1, wherein bonding of the compound α to the substrate is obtained.

7. The surface treatment method according to claim 6, wherein the bonding is obtained by chemical reaction of the compound α to the substrate and/or physical absorption of the compound α by the substrate.

* * * * *

UNITED STATES PATENT AND TRADEMARK OFFICE
CERTIFICATE OF CORRECTION

PATENT NO. : 9,790,242 B2
APPLICATION NO. : 14/406679
DATED : October 17, 2017
INVENTOR(S) : Kunio Mori et al.

Page 1 of 1

It is certified that error appears in the above-identified patent and that said Letters Patent is hereby corrected as shown below:

On the Title Page

Item (73), the Assignees' information is incorrect. Item (73) should read:
--(73) Assignees: Kunio Mori, Morioka-shi (JP); Sulfur Chemical Laboratory, Inc., Morioka-shi (JP); Meiko Electronics Co., Ltd., Ayase-shi (JP)--

Signed and Sealed this
Seventeenth Day of April, 2018

Andrei Iancu
*Director of the United States Patent and Trademark Office*